(12) United States Patent
Omori et al.

(10) Patent No.: US 8,828,212 B2
(45) Date of Patent: Sep. 9, 2014

(54) DIELECTRIC CYTOMETRIC APPARATUS AND DIELECTRIC-CYTOMETRIC CELL SORTING METHOD

(75) Inventors: Shinji Omori, Tokyo (JP); Kazumasa Sato, Tokyo (JP); Yoichi Katsumoto, Tokyo (JP); Tomoyuki Umetsu, Tokyo (JP); Yoshihito Hayashi, Chiba (JP)

(73) Assignee: Sony Corporation, Tokyo (JP)

( * ) Notice: Subject to any disclaimer, the term of this patent is extended or adjusted under 35 U.S.C. 154(b) by 205 days.

(21) Appl. No.: 13/278,749

(22) Filed: Oct. 21, 2011

(65) Prior Publication Data

US 2012/0103817 A1    May 3, 2012

(30) Foreign Application Priority Data

Oct. 29, 2010   (JP) ................................. 2010-243765

(51) Int. Cl.
| | | |
|---|---|---|
| *B03C 5/02* | (2006.01) | |
| *B03C 5/00* | (2006.01) | |
| *B01L 3/00* | (2006.01) | |
| *G01N 15/12* | (2006.01) | |
| *G01N 15/10* | (2006.01) | |

(52) U.S. Cl.
CPC ......... *G01N 15/12* (2013.01); *B01L 2300/0864* (2013.01); *B01L 2400/0424* (2013.01); *B01L 2300/0816* (2013.01); *B01L 2200/0652* (2013.01); *B03C 5/005* (2013.01); *B01L 3/502761* (2013.01); *G01N 2015/1081* (2013.01); *B03C 5/028* (2013.01); *B01L 2300/0645* (2013.01)
USPC .......................................... 204/643; 204/547

(58) Field of Classification Search
CPC ........... G01N 33/4915; G01N 15/12–15/1484; G01N 2015/10–2015/1497
USPC ................................................ 204/643, 547
See application file for complete search history.

(56) References Cited

U.S. PATENT DOCUMENTS

| | | | |
|---|---|---|---|
| 2,656,508 A | 10/1953 | Coulter | |
| 3,502,974 A | 3/1970 | Coulter et al. | |

(Continued)

FOREIGN PATENT DOCUMENTS

| | | |
|---|---|---|
| JP | 2003-507739 | 2/2003 |
| JP | 2003-287519 | 10/2003 |

(Continued)

OTHER PUBLICATIONS

S. Gawad et al., "Micromachined impedance spectroscopy flow cytometer for cell analysis and particle sizing," The Royal Society of Chemistry, Lab on a Chip, 2001, vol. 1, pp. 76-82. (7 pages).

(Continued)

*Primary Examiner* — J. Christopher Ball
(74) *Attorney, Agent, or Firm* — K&L Gates LLP

(57) ABSTRACT

Disclosed herein is a dielectric cytometric apparatus capable of analyzing cells and sorting the cells without adopting an optical analysis method and provides a dielectric cytometric cell sorting method for the apparatus. A stenosis channel allowing a single cell to flow is created on a cell injection section of a micro flow channel device used as a portion of the dielectric cytometric apparatus. A pair of measurement electrodes is created on the stenosis channel and an analyzer connected to the measurement electrodes measures the complex dielectric constant of for every cell passing through the stenosis channel. A electric-field application section provided on the downstream side of the stenosis channel applies an electric field for changing the flow of the cells inside a flow channel on the basis of information on the measured complex dielectric constants so that the cells can be sorted by making use of branch channels.

6 Claims, 15 Drawing Sheets

(56) References Cited

U.S. PATENT DOCUMENTS

| | | | |
|---|---|---|---|
| 5,993,630 | A | 11/1999 | Becker et al. |
| 6,204,668 | B1 | 3/2001 | Sequeira et al. |
| 6,431,551 | B1 | 8/2002 | Fuse et al. |
| 7,294,249 | B2 | 11/2007 | Gawad et al. |
| 2005/0114041 | A1 | 5/2005 | Gawad et al. |
| 2008/0221805 | A1 | 9/2008 | Andrews |
| 2009/0026080 | A1 | 1/2009 | Han et al. |

FOREIGN PATENT DOCUMENTS

| | | |
|---|---|---|
| JP | 2009-525862 | 7/2009 |
| JP | 2010-181399 | 8/2010 |

OTHER PUBLICATIONS

Karen Cheung et al., "Impedance Spectroscopy Flow Cytometry: On-Chip Label-Free Cell Differentiation," Cytometry Part A 65A, 2005, pp. 124-132. (9 pages).

European Patent Office, Extended European Search Report issued in connection with European Patent Application No. 11008237.7, dated May 3, 2013. (8 pages).

Japanese Patent Office, Grounds for refusal notice issued in connection with Japanese Patent Application No. 2010-243765, dated Mar. 11, 2014. (4 pages).

Japanese Patent Office, Grounds for refusal notice issued in connection with Japanese Patent Application No. 2010-243765, dated Jun. 3, 2014. (3 pages).

F I G . 1
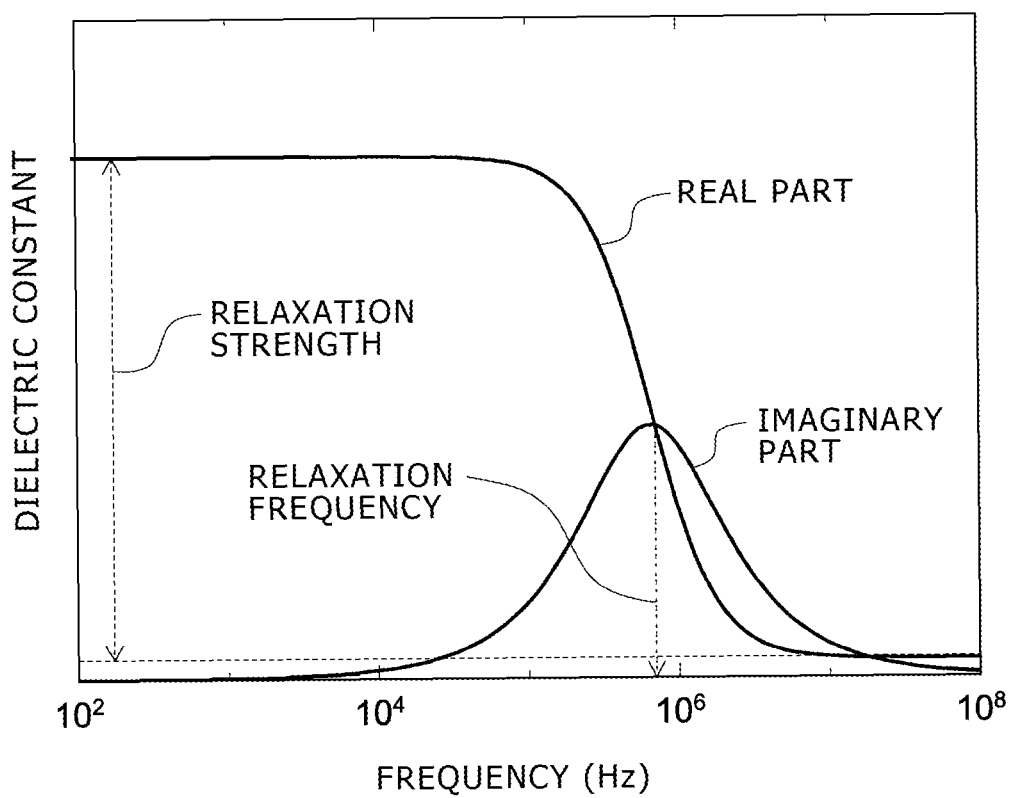

| AN | COMPLEX RESISTANCE ANALYZER | MFs | SORTING FLOW CHANNEL |
| --- | --- | --- | --- |
| TR | SORTING SIGNAL GENERATOR | D | WASTE SOLUTION DISPOSAL |
| SC | SORTING MECHANISM | S1,..., Sn | CELL ACCUMULATOR |
| MFa | ANALYSIS FLOW CHANNEL | | |

DIELECTRIC CYTOMETRIC APPARATUS AND DIELECTRIC-CYTOMETRIC CELL SORTING METHOD

PRIORITY CLAIM

The present application claims priority to Japanese Priority Patent Application JP 2010-243765 filed in the Japanese Patent Office on Oct. 29, 2010, the entire contents of which is hereby incorporated by reference.

BACKGROUND

The present disclosure relates to a dielectric cytometric apparatus for analyzing and sorting cells as well as a dielectric cytometric cell sorting method.

In the fields of life sciences and medical researches or in the fields of medical cares such as clinical practices, an analysis method referred to as flow cytometry is adopted. In the flow cytometry, liquid composed of cells individually freed from each other is taken as a sample. Under a dilute condition with an inter-cell average distance sufficiently greater than the dimensions of the cell, liquid serving as a sample is driven in to flow through the inside of a flow channel pipe. A signal detection section installed in the flow channel pipe carries out a certain analysis/measurement on individual cells flowing through the signal detection section. Cells having measured signals approximating each other are considered to be cells of the same type. Thus, signals measured for a number of cells included in the sample liquid are analyzed in order to identify the type of cells included in a cell group serving as the sample and calculate a cell-type cell count representing the number of cells included in the cell type. Instead of calculating the number of cells included in the cell type, it is also possible to calculate a ratio of the cell-type cell count to the total number of cells. The analysis method adopted in the flow cytometry is classified into large categories, that is, an optical analysis method and an electrical analysis method.

As the optical analysis method, a combination of only a fluorescent detection method and a light scattering detection method is adopted. The principle of the fluorescent detection method is explained as follows.

On the surface of a cell, there are protein molecules each referred to as a surface antigen. The surface antigen is by no means limited to one type. Thus, by identifying the type of the surface antigen and the number of surface antigens included in the type of the antigen, it is possible to identify the cell type to which the cells pertain. If the surface-antigen molecules are known, it is possible to synthesize molecules, which are specifically joinable to the surface-antigen molecules, to the surface-antigen molecules. The molecules specifically joinable to the surface-antigen molecules are referred to as antibody molecules for the surface antigens. In addition, it is also possible to chemically join fluorescent labeling molecules to the antibody molecules. A fluorescent labeling molecule is a molecule which generates fluorescent light if light having a wavelength in a specific wavelength band is radiated to the molecule. That is to say, fluorescent labeling antibodies generating fluorescent light beams having different wavelengths are each synthesized with a surface antigen molecule used for characterizing the cell type assumed to be included in a cell group serving as a subject of an analysis. The composite of all these fluorescent labeling antibodies is taken as a labeling test reagent. If this labeling test reagent is added to liquid solution, each of cells of the labeling test reagent is labeled with a fluorescent molecule which varies from cell type to cell type to which the cells pertain.

In a signal detection section installed in a flow channel pipe of a flow cytometric apparatus also referred to as a flow cytometer, laser light is radiated to a cell passing through the signal detection section. When laser light is radiated to such cells, the surface-antigen molecules of individual cells and fluorescent labeling molecules joined to antibody molecules specifically joined to the surface-antigen molecules are excited, generating fluorescent light having a wavelength peculiar to the fluorescent labeling molecules. For a number of cells, the fluorescent light is detected in order to count the number of cells for every cell type. This method is adopted widely. As a matter of fact, the so-called flow cytometry is intended to imply essentially this method.

The flow cytometer put into the market is used not only for obtaining the existing state of surface antigen molecules but also additional information such as cell dimensions and the internal density of the cells. Thus, the flow cytometer is used for measuring the strength of laser light scattered by cells at the same time.

An electrical method has been put to practical use as the method of a Coulter counter. For more information on this Coulter counter, the reader is advised to refer to documents such as U.S. Pat. No. 2,656,508. In the Coulter counter, a pair of electrodes are provided on a signal detection section inside a flow channel pipe. A voltage is applied between the electrodes. When an individual cell passes through the space between the electrodes, the resistance of the space changes. A frequency at which the resistance changes is measured in order to count the number of cells passing through the signal detection section. In addition, the magnitude of the change of the resistance is approximately proportional to the volume of the cell. Thus, if a cell group serving as the object of the analysis includes cells of different types having dimensions much different from each other, the operation to count the number of cells can be carried out for each of the cell types.

As an improved technology of the Coulter counter, there has been proposed a technology of superposing an AC (Alternating Current) voltage having a frequency of tens of MHz on a DC (Direct Current) voltage applied between the electrodes. For more information on this improved technology, the reader is advised to refer to documents such as U.S. Pat. Nos. 3,502,974 and 6,204,668. As is commonly known, there is a correlation between the AC resistance of the cell at frequencies of tens of MHz and the internal density of the cell. By obtaining measured data for each of the AC and DC resistances, a detailed analysis can be conducted in comparison with the existing methods.

The electrical analysis method based on only a DC resistance or a combination of a DC resistance and an AC resistance is used in some flow cytometers by combining the electrical analysis method with the optical analysis method. In addition, in the clinical examination field, there is used an automatic blood-cell counting apparatus for counting, among others, the number of red-blood cells, the number of white-blood cells and the number of blood platelets. Normally, the automatic blood-cell counting apparatus is differentiated from the flow cytometer. From the standpoint of the operation principle of the automatic blood-cell counting apparatus, however, the automatic blood-cell counting apparatus can be said to be a flow cytometer in a broader sense. In this specification, without differentiating the automatic blood-cell counting apparatus and the flow cytometer from each other, the technical term "flow cytometer" is used to imply both the automatic blood-cell counting apparatus and the automatic blood-cell counting apparatus which is a flow cytometer in a broader sense.

As described above, in the present state of the art, the flow cytometer adopting the electrical analysis method is implemented by adopting also the optical analysis method.

Next, a cell sorting technology adopted by the flow cytometer is explained.

Applications include not only analyses of cells included in liquid solution, but also possibly sorting of only cells included in a specific cell type from other cells by making use of results of the analyses. For example, there is a case in which a cell type appearing in peripheral blood exists due to a sort of blood cancer. In this case, only the cell type is sorted and a gene analysis or a protein analysis is carried out on the cell type. By conducting such an analysis, it is quite within the bounds of possibility that a clue as to what has caused the blood-cancer disease is obtained. For example, the clue may suggest that the blood-cancer disease has been caused by a gene abnormality or the like. As another example, in an attempt to induce an iPS cell from a cell of a human being, not every cell of the human being is induced into an iPS cell. It is thus necessary to sort only iPS cells from cultured cells.

In these cases, it is necessary to provide a mechanism for sorting only specific cells in accordance with a signal generated by a signal detection section provided in the flow channel pipe on the downstream side of the signal detection section. This mechanism is referred to as a sorter. The sorter is provided in upper-level models of the flow cytometer put into the market.

If a cell sorted by a fluorescent flow cytometer is used for a research purpose, a big problem is raised. In this case, the fluorescent flow cytometer is a flow cytometer based on a fluorescent detection method selected among optical analysis methods. The big problem is that, strictly speaking, the original state of the cell used as the subject of control is different from the state of a fluorescently labeled cell. If an antibody molecule is joined to a surface antigen molecule, chemical excitement is added to the inside of the cell so that a multistage signal transmission reaction may probably take place. However, the effect of such a small change can be regarded as a small effect so that the cell can be normally used for a research purpose.

It is to be noted that, as a technology related to the present disclosure, there has been proposed a technology for measuring a dielectric spectrum of every cell and, on the basis of the result of the measurement, cells are sorted. For more information on this technology, the reader is advised to refer to document such as Japanese Patent Laid-open No. 2010-181399. Additionally, the reader is suggested to refer to document such as JP-T-2003-507739.

SUMMARY

In the fields of the regenerative medical care and the cell medical care, after some biochemical processes have been carried out on cells sorted from the blood of a patient, the obtained cell system may be re-implanted to the inside of the body of the patient for the purpose of a medical care. Typical examples of the biochemical process are a culturing process, an activation process and a differentiation induction process. However, no safety is assured for the operation to re-implant cells in which fluorescent labeling antibody molecules have been rejoined to surface antigen molecules or re-implant a system of cells derived from such cells to the inside of the body of the patient. It is thus desirable to provide a technology capable of analyzing cells and sorting cells by sustaining the original living state of the cells as it is without labeling the cells.

The electrical analysis method does not require a labeling substance. Thus, by adoption of the electrical analysis method in a sorting apparatus, the cell sorting apparatus can be used for the purposes of a regenerative medical care and a cell medical care. In the existing Coulter counter, however, it is possible to obtain only limited measured data based on only a DC resistance or a combination of a DC resistance and an AC resistance. Thus, a capability demonstrated by the Coulter counter as a capability of sorting different cell types is so inadequate. As a matter of fact, there is not a cell sorter adopting only the electrical analysis method without adopting the optical analysis method.

Under these circumstances in the art, it is desirable to provide a dielectric cytometric apparatus capable of analyzing and sorting cells without adopting the optical analysis method and a dielectric cytometric cell sorting method to be adopted by the dielectric cytometric apparatus.

In order to achieve the desire described above, in accordance with an embodiment of the present disclosure, there is provided a dielectric cytometric apparatus employing a flow channel, a first electrode pair, an analysis unit, a second electrode pair and a cell sorting unit.

The flow channel includes a stenosis channel through which a single cell is capable of flowing and branch channels provided on the downstream side of the stenosis channel as branch channels for sorting cells included in liquid flowing through the flow channel.

The first electrode pair to which an AC voltage is applied is capable of generating an AC electric field on the stenosis channel.

By generating the AC electric field generated on the stenosis channel by the AC voltage applied to the first electrode pair, the analysis unit is capable of measuring a complex dielectric constant depending on the cell for each of the cells each flowing through the stenosis channel.

The second electrode pair to which a voltage is applied is capable of generating an electric field on a flow-channel portion on the downstream side of the stenosis channel but on the upstream side of the branch channels.

By generating the electric field on the flow-channel portion by the voltage applied to the second electrode pair, on the basis of the complex dielectric constant measured by the analysis unit, the cell sorting unit is capable of providing a dielectrophoretic force to the cells and sorting the cells by making use of the branch channels.

As described above, for every cell passing through the stenosis channel of the flow channel, the analysis unit measures a complex dielectric constant depending on the cell and, on the basis of a signal based on the complex dielectric constant, the cell sorting unit sorts the cells by making use of a dielectrophoretic force generated by an electric field created on the downstream side of the stenosis channel. That is to say, the dielectric cytometric apparatus is capable of both electrically analyzing (or measuring) and electrically sorting cells without adoption of the optical analysis method.

In addition, it is possible to provide a configuration in which, as a signal of the AC voltage applied to the first electrode pair, the analysis unit generates a superposed voltage signal including a superposed AC voltage having a plurality of frequencies and carries out a Fourier transform on signals of a voltage and a current, which are measured when the single cell passes through the stenosis channel, in order to calculate the complex dielectric constant for every one of the frequencies. In this present disclosure, a superposed voltage signal including a superposed AC voltage having a plurality of frequencies, that is, a multi-point frequency, is applied to the first electrode pair and a Fourier transform is carried out in order to obtain a frequency spectrum distribution for every cell.

In addition, it is possible to provide a configuration in which the analysis unit stores in advance reference information to be used as a reference of the complex dielectric constant measured for every cell. In this configuration, the cell sorting unit refers to the complex dielectric constant measured by the analysis unit and the reference information on a real-time basis and creates the electric field on the basis of information indicating whether or not the complex dielectric constant is within the range of the reference information. By storing the reference information in advance, after storing the reference information, it is possible to provide the cell sorting unit with a signal based on the measured complex dielectric constant to serve as a signal used for sorting cells through execution of open-loop (feed-forward loop) control.

A dielectric cytometric cell sorting method according to another embodiment of the present disclosure includes the step of causing fluid including cells to flow through a flow channel including a stenosis channel and branch channels.

An AC electric field is created on the stenosis channel.

For each of the cells passing through the stenosis channel, a complex dielectric constant depending on the cell is measured.

On the basis of the measured complex dielectric constant, an electric field is created on a flow-channel portion on the downstream side of the stenosis channel but on the upstream side of the branch channels in order to apply a dielectrophoretic force to the cells so that the cells can be sorted by making use of the branch channels.

As described above, a complex dielectric constant is measured for every cell passing through the stenosis channel of the flow channel and a dielectrophoretic force is generated by an electric field created on a flow-channel portion on the downstream side of the stenosis channel but on the upstream side of the branch channels on the basis of the measured complex dielectric constant and applied to cells so that the cells can be sorted by making use of the branch channels. That is to say, it is possible to carry out a process of both analyzing (or measuring) and sorting cells electrically without adoption of the optical analysis method.

In accordance with the embodiments of the present disclosure, it is possible to carry out a process of both analyzing (or measuring) and sorting cells electrically without adoption of the optical analysis method.

BRIEF DESCRIPTION OF THE FIGURES

FIG. 1 is a graph representing models of dispersions of a complex dielectric constant;

FIG. 8 is a set of histograms showing $\Delta C$ representing a relaxation amplitude and a critical frequency fc at which the relaxation occurs;

DETAILED DESCRIPTION

Figure 2:
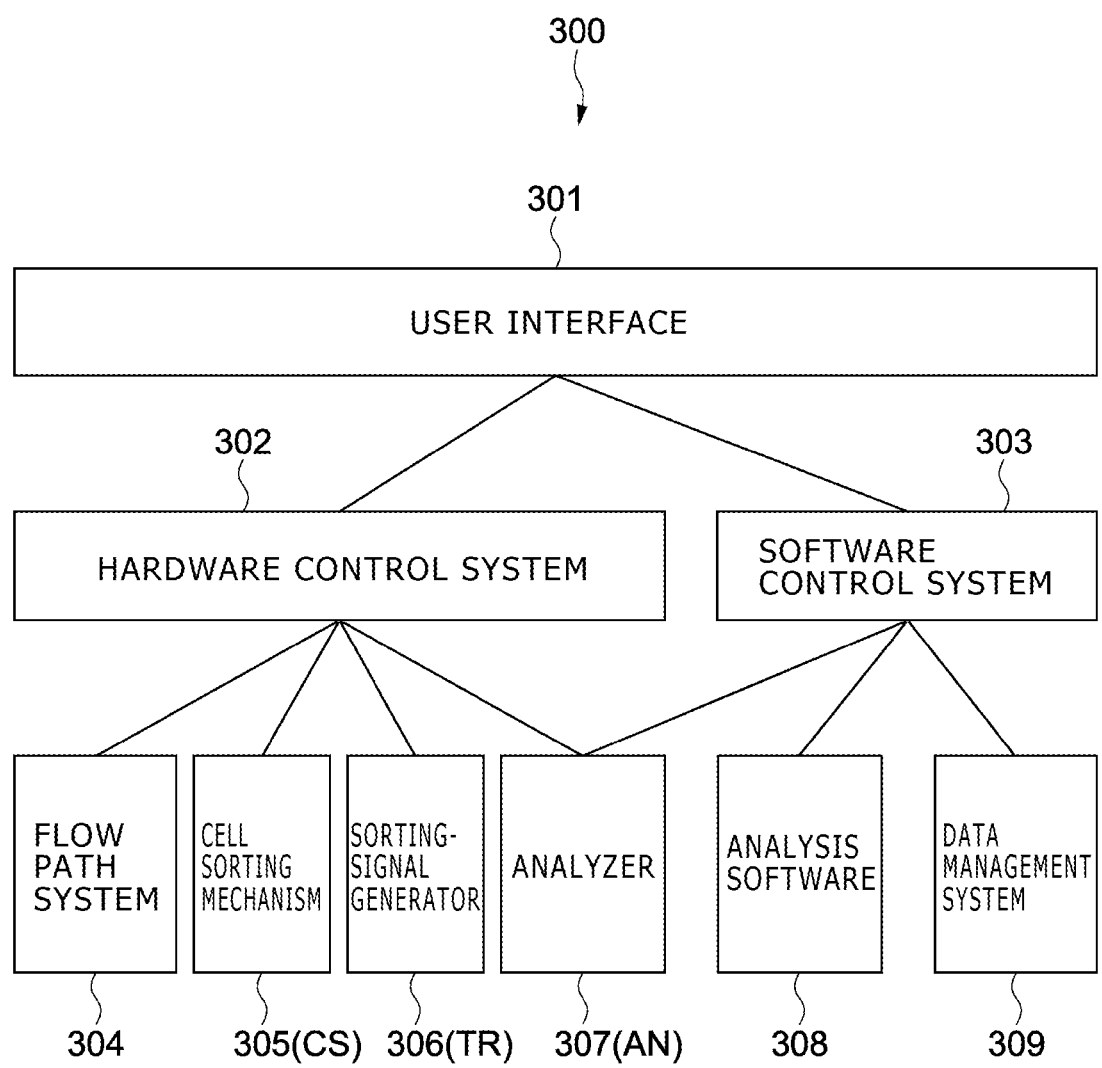
FIG. 2 is a block diagram showing the entire configuration of a dielectric spectro cytometric apparatus according to one mode of the present disclosure.

The present disclosure is described below in greater detail with reference to the drawings according to an embodiment.

[1] Explanation of the dispersion of the complex dielectric constant of a cell

[2] Explanation of the concept or principle of a dielectric spectro cytometric apparatus and an analysis conducted by making use of the apparatus on the basis of a multi-point frequency

[3] Explanation of concrete embodiments of the dielectric spectro cytometric apparatus

[1] Explanation of the Dispersion of the Complex Dielectric Constant of a Cell

Suspension liquid including cells is injected into a measurement container having the shape resembling a parallel-plate capacitor composed of a pair of electrode plates facing each other. An AC voltage is applied between the electrode plates and a current flowing due to the application of the AC voltage is measured in order to find a complex resistance (or a complex impedance) between the electrode plates. If the frequency of the AC voltage is changed, the measured complex resistance also changes. The complex resistance can be measured by making use of a precise impedance analyzer put into the market.

The complex resistance found in this way as a complex resistance depending on the frequency can be converted into the complex dielectric constant of the suspension liquid including cells by correcting some factors such as a factor depending on the shape of the measurement container and a factor depending on the transmission characteristic of an electrical wire connecting the complex-resistance measuring apparatus to the measurement container. For more information on this conversion, the reader is advised to refer to a publication authored by Tetsuya Hanai and published by Yoshioka Bookstore with a title of "Heterogeneous Structures and Dielectric Constants." The frequency-dependent characteristic of the complex resistance is referred to the dispersion of the complex resistance or a dielectric constant spectrum. FIG. 1 is a graph representing models of dispersions of a complex dielectric constant.

For frequencies in a range not higher than about 0.1 MHz, the real part of the relaxation of the complex dielectric constant for the cell suspension liquid has about a constant value independent of the frequency. As the frequency is increased, this real part considerably decreases in the so-called dielectric relaxation phenomenon in a frequency area around about 1 MHz. If the frequency is further increased, the real part has an all but constant small value. On the other hand, the imaginary part of the relaxation of the complex dielectric constant has a frequency characteristic with a peak value in the frequency area in which the dielectric relaxation phenomenon occurs.

As generally known, the dispersion of the complex dielectric constant of the suspension liquid can be expressed by a single relaxation function such as a Cole-Cole function or expressed by superposition of a plurality of relaxation functions. For an experimentally obtained dispersion of the complex dielectric constant, by carrying out non-linear fitting to treat unknown coefficients of the relaxation function as variables, the variables can be optimized. In the case of the Cole-Cole function for example, variables characterizing a dispersion curve include a relaxation strength and a relaxation frequency. These dielectric variables are closely related to the structure and physicality of the cell. Japanese Patent Laid-open No. 2009-42141 discloses a method for inferring the electrical physicality value of a facet composing a cell from a complex dielectric constant. In this case, the facet composing a cell represents, among others, a cell film and cell properties.

[2] Explanation of the Concept or Principle of a Dielectric Spectro Cytometric Apparatus and an Analysis Conducted by Making Use of the Apparatus on the Basis of a Multi-point Frequency

[The Entire Configuration of the Dielectric Spectro Cytometric Apparatus]

FIG. 2 is a block diagram showing the entire configuration of a dielectric spectro cytometric apparatus 300 as an embodiment of the dielectric cytometric apparatus according to the present disclosure.

Conceptually, the dielectric spectro cytometric apparatus 300 is configured to have three stage layers. First of all, the stage layer on the top is a user interface 301. The user interface 301 is provided between the user and the main body of the dielectric spectro cytometric apparatus 300. The user interface 301 plays the role to receive information entered by the user to the dielectric spectro cytometric apparatus 300 and show a measurement result generated by the dielectric spectro cytometric apparatus 300 to the user. A typical example of the information entered by the user is measurement conditions. The user interface 301 is physically implemented by a terminal of a computer and a program invoked in the computer.

Below the user interface 301, a hardware control system 302 and a software control system 303 are provided.

The hardware control system 302 is hardware for controlling configuration elements of the dielectric spectro cytometric apparatus 300, carrying out measurements and recording measured data. The hardware control system 302 also includes programs to be executed for controlling the configuration elements of the dielectric spectro cytometric apparatus 300, carrying out measurements and recording measured data. To be more specific, the hardware control system 302 is hardware for controlling a flow channel system 304, a cell sorting mechanism 305, a sorting-signal generator 306 and an analyzer 307. It is a main object of flow channel system 304 to introduce a cell used as a sample into a signal detection section. The analyzer 307 is an analyzer for measuring a signal caused by the introduced cell. Conceptually, the analyzer 307 includes a complex analyzer AN to be described later. The sorting-signal generator 306 is a generator for generating a signal used for sorting cells whereas the cell sorting mechanism 305 is a mechanism for sorting the cells on the basis of the signal generated by the sorting-signal generator 306.

On the other hand, the software control system 303 has analysis software 308 and a data management system 309. The data management system 309 is a system for managing and saving the recorded measured data received from the analyzer 307. The data management system 309 includes a data management program and a data server. The analysis software 308 is software for extracting meaningful information from the measured data.

The hardware control system 302, the software control system 303 and the analyzer 307 collaborate with each other to function as an analysis unit. In addition, the hardware control system 302 and the sorting-signal generator 306 collaborate with each other to function as a cell sorting unit.

[Flow Channel System]

Figure 3:
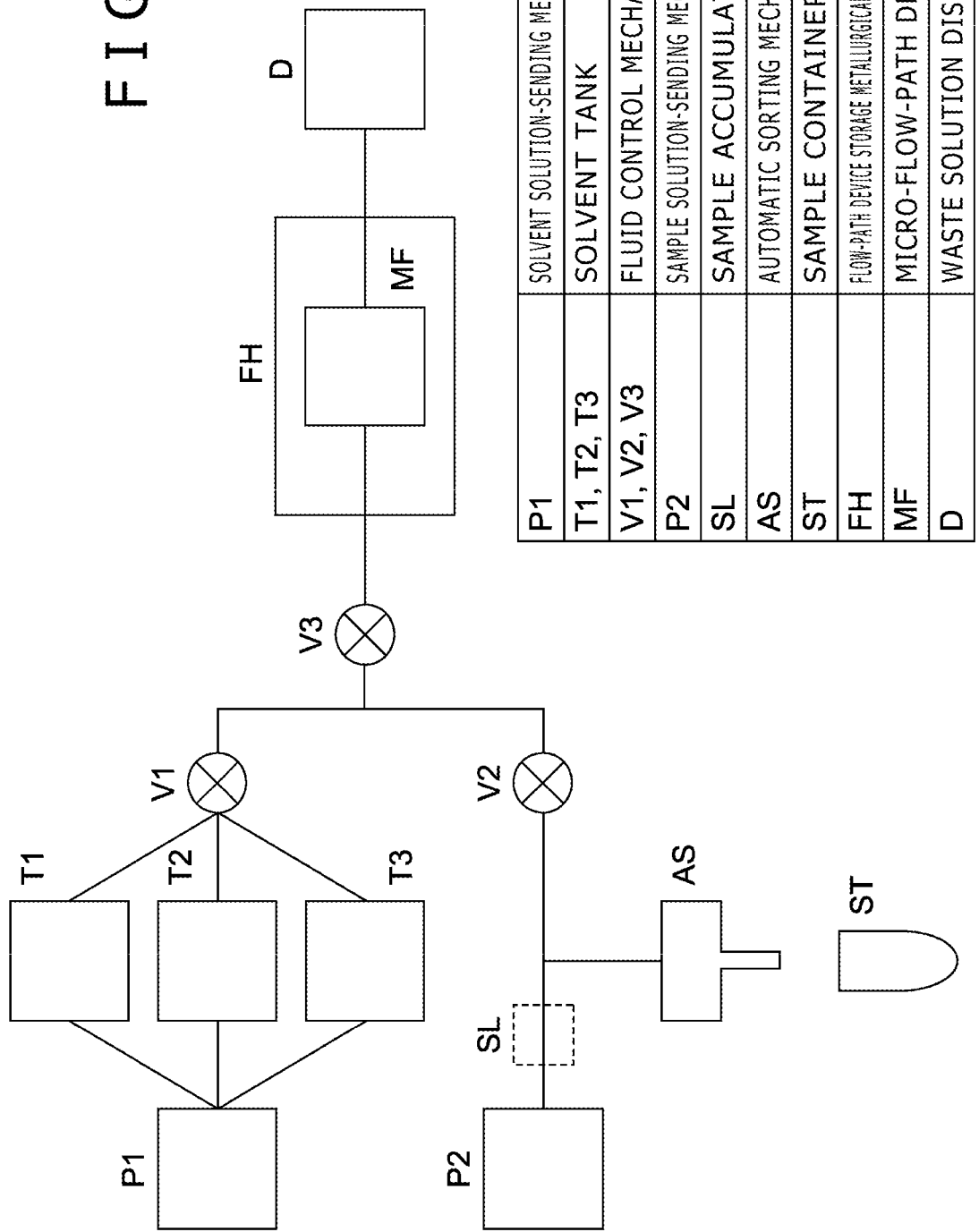
FIG. 3 is a block diagram showing the configuration of a flow channel system included in the dielectric spectro cytometric apparatus shown in FIG. 2.

FIG. 3 is a block diagram showing the configuration of the flow channel system 304 included in the dielectric spectro cytometric apparatus 300 shown in FIG. 2.

As shown in FIG. 3, the flow channel system 304 has a micro flow channel device MF for detecting a signal and other sections referred to as fluid control mechanisms V1, V2 and V3. Due to operations of the fluid control mechanisms V1, V2 and V3, liquid solution is introduced into the micro flow channel device MF from an external source and, after a complex resistance has been measured by the signal detection section, the liquid solution is discharged back to the external source. Serving as a sample, the liquid solution is fluid including cells. It is to be noted that, conceptually, the liquid solution includes dispersion liquid or suspension liquid. The technical term 'liquid solution' used in the following description conceptually includes dispersion liquid or suspension liquid.

Elements composing each of the fluid control mechanisms V1, V2 and V3 typically include a container (or a tank), a compressed-air supplier (or a compressor), a pump, a valve and a pipe. The container (or the tank) is an element for accumulating dispersion solvent and/or cleaning liquid whereas the compressed-air supplier (or a compressor) is en element for pressing liquid solution. The pump is an element for sucking sample liquid solution and introducing the sample liquid solution into the micro-flow-channel device MF. The valve is an element for controlling the flow of liquid solution whereas the pipe is an element for connecting elements to each other.

It is an object of the flow channel system 304 to smoothly introduce a sample into the micro flow channel device MF. However, the elements composing the flow channel system 304 are by no means limited to the elements described above. That is to say, other elements can be used for constructing the flow channel system 304 as long as the other elements are capable of achieving the object of the flow channel system 304. The cell liquid solution is injected into a sample tank ST which is provided inside the dielectric spectro cytometric apparatus 300.

When a measurement is started, first of all, a flow channel pipe for receiving a sample is adjusted. Liquid solvent tanks T1, T2 and T3 typically contain pure water, PBS buffering liquid or cleaning liquid such as SDS liquid solution. The number of tanks and the type of the solvent are by no means limited to these examples. A solvent solution-sending mechanism P1 sends liquid in order to properly drive the fluid control mechanisms V1 and V3. Thus, a flow channel pipe including the micro flow channel device MF mounted on a storage metallurgical apparatus FH is cleaned and then filled up with the PBS buffering liquid.

Next, an automatic sample sorting mechanism AS absorbs a sample having a proper quantity from the sample tank ST. The sample is pulled in a sample accumulator SL which is referred to as the so-called sample loop. The sample accumulator SL is not element provided specially but, in actuality, a part of the flow channel pipe. A sample solution-sending mechanism PS sends the sample in the sample accumulator SL to the micro flow channel device MF. By properly operating the fluid control mechanisms V1 and V3, the sample is capable of flowing through the micro flow channel device MF and exhausted to a waste solution disposal D.

After the measurement has been ended, the pipe is cleaned in accordance with the same fluid control procedure as the adjustment which has been carried out prior to the injection of the sample as the adjustment of the flow channel pipe.

Figure 4:
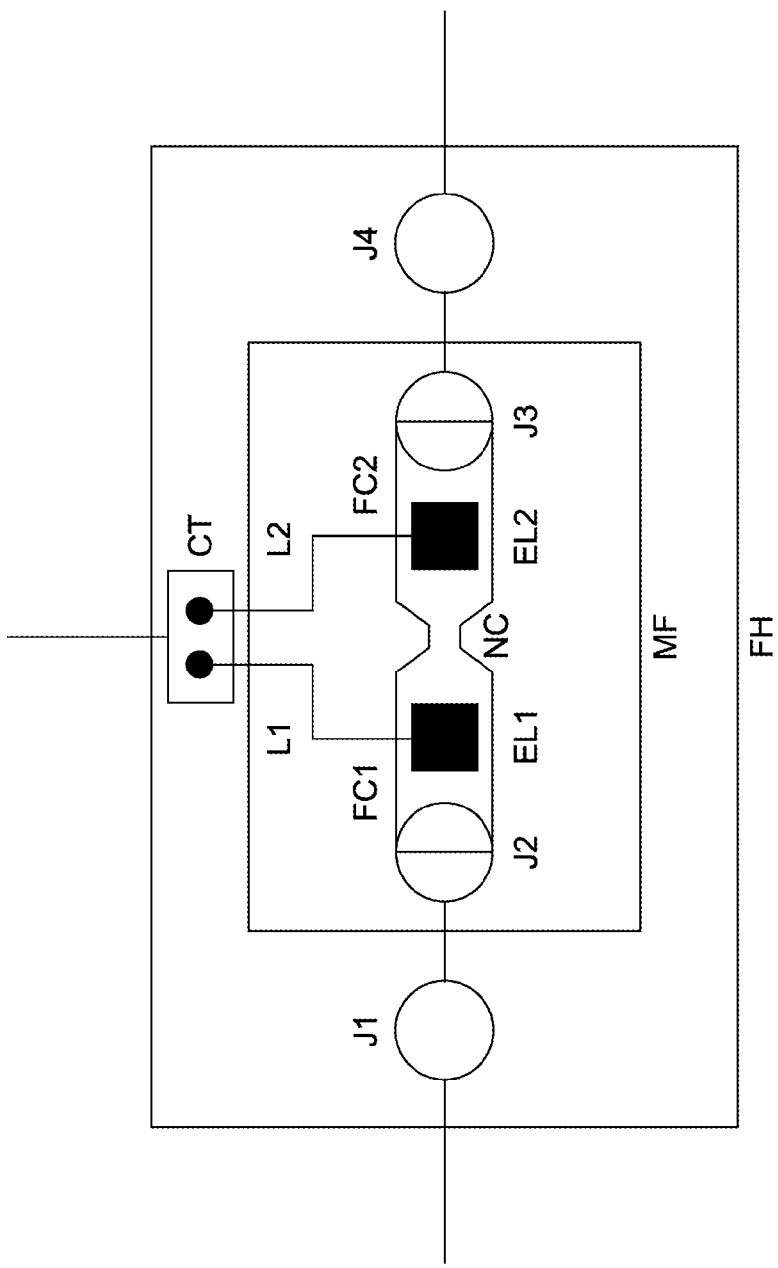
FIG. 4 is a block diagram showing the configuration of a micro-flow-channel device.

FIG. 4 is a block diagram showing the configuration of the micro-flow-channel device MF.

The micro flow channel device MF is connected fluidically to an external flow channel pipe and connected electrically to an external complex-resistance analyzer. The complex-resistance analyzer can be a portion or all of the analyzer 307 employed in the dielectric spectro cytometric apparatus 300 shown in FIG. 2. As described above, the micro flow channel device MF is mounted on the storage metallurgical apparatus FH which implements the connections between the micro flow channel device MF and the external flow channel pipe as well as between the micro flow channel device MF and the external complex-resistance analyzer.

A proper structure of the micro flow channel device MF used in this embodiment and a proper method for manufacturing the micro flow channel device MF are disclosed in Japanese Patent Laid-open No. 2010-181399 and Japanese Patent Laid-open No. 2008-279382 respectively. Inside each of flow channels FC1 and FC2 each having dimensions sufficiently greater than the dimensions of a cell, a pair of electrodes EL1 and EL2 are formed. Between the electrodes EL1 and EL2 forming a pair, a member NC having dimensions of about the same order as the dimensions of a cell is provided. The member NC is the stenosis channel described earlier. Since the electrical resistance of the stenosis channel NC is very large in comparison with those of the flow channels FC1 and FC2, most of a voltage applied between the electrodes EL1 and EL2 forming a pair is virtually applied to only the stenosis channel NC. Thus, even if the electrodes EL1 and EL2 forming a pair are spatially separated from each other, the stenosis channel NC functions as the signal detection section mentioned before. Details of the principle are described in Japanese Patent Laid-open No. 2010-181399. This principle will be explained later too.

The flow channel FC1 is connected to a flow channel pipe created in the storage metallurgical apparatus FH by proper joining section J2. By the same token, the flow channel FC2 is connected to the flow channel pipe created in the storage metallurgical apparatus FH by proper joining section J3. A typical example of the proper joining sections J2 and J3 is an O ring. The storage metallurgical apparatus FH is connected to an external pipe by proper joining sections J1 and J4. A typical example of the proper joining sections J1 and J4 is a pipe joining component of the liquid chromatography. In addition, the electrodes EL1 and EL2 forming a pair are connected to the outside of the micro flow channel device MF by pull-out wires L1 and L2 respectively. The electrodes EL1 and EL2 forming a pair are also connected to a complex-resistance analyzer through proper connection components.

[Measurement System (Analyzer)]

Figure 5:
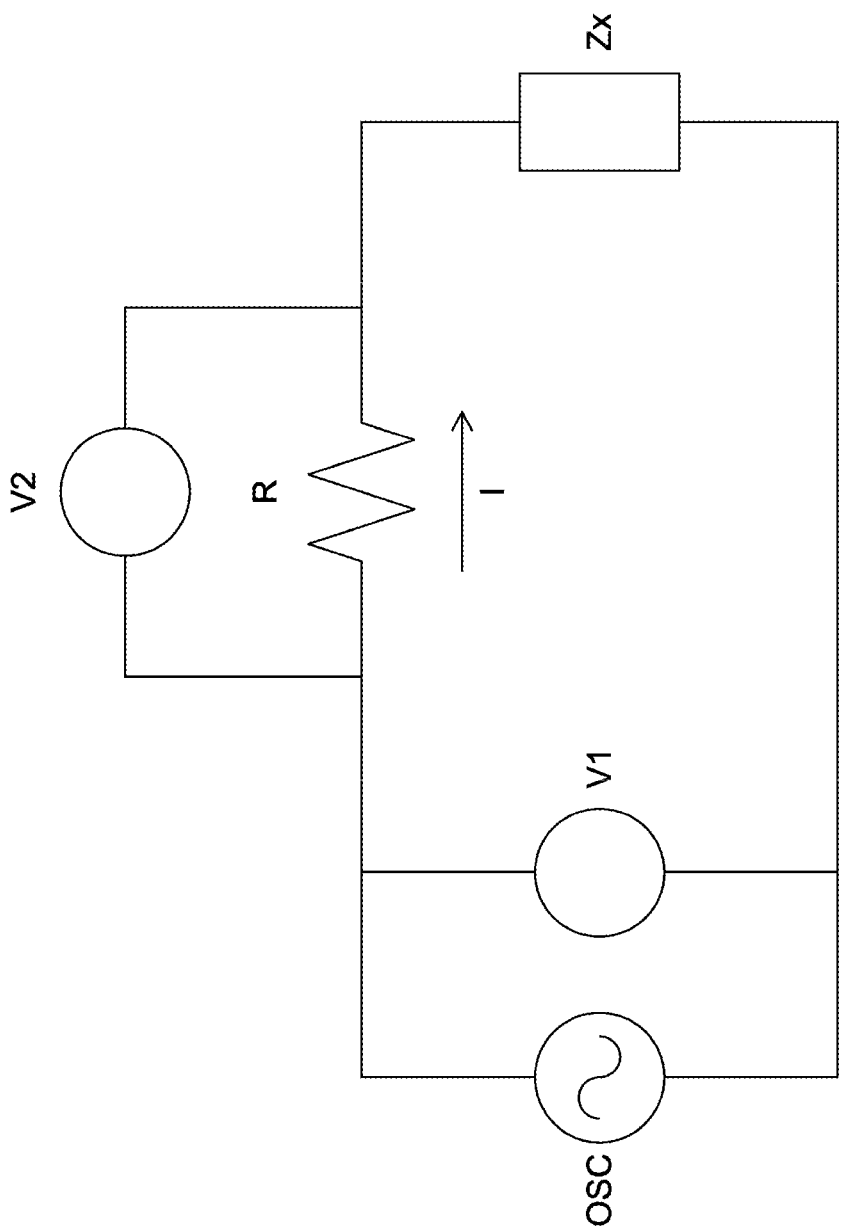
FIG. 5 is a diagram showing a circuit for implementing a IV method for measuring a complex resistance.

The basic circuit for measuring a complex resistance is known widely. FIG. 5 is a diagram showing a circuit for implementing a IV method for measuring a complex resistance.

An oscillator OSC employed in the circuit shown in the figure is a section for generating a voltage having a sinusoidal waveform. The voltage applied to the sample is measured by a voltage measurement circuit V1. Since a current I flowing through the sample cannot be measured directly, a voltage measurement circuit V2 is used for measuring a voltage appearing between the two ends of a resistor R having a known low resistance. Thus, the current I flowing through the sample can be computed from the voltage appearing between the two ends of the resistor R. In order to eliminate the effect of the low-resistance resistor R on the measurement, the low-resistance resistor R may be replaced by a device generating a small loss. The complex resistance Zx of the sample can be found from the following equation:

$$Zx=(V1/I)=(V1/V2)R$$

However, the principle of the dielectric spectro cytometry cannot be readily implemented by making use of such commonly known knowledge. This is because both the amplitude of a very small resistance change and the phase of the change must be measured within a short period of time for a multi-point frequency range. The very small resistance change is a change caused by a single cell passing through the stenosis channel NC serving as the signal detection section.

The following description explains an embodiment provided by the present disclosure to serve as an embodiment for implementing such a limitation imposing measurement of a complex resistance.

Figure 6:
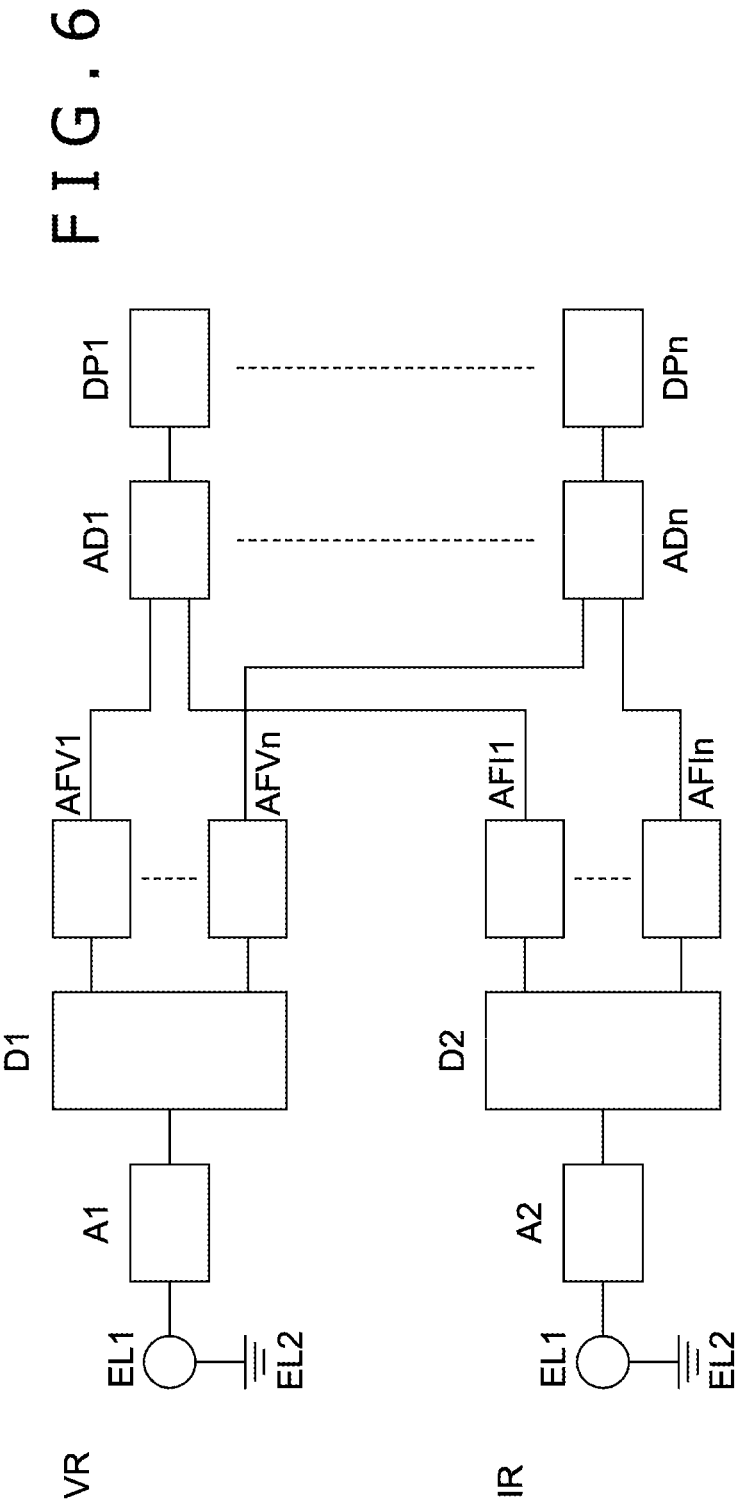
FIG. 6 is a diagram showing an embodiment implementing a measurement circuit for measuring the complex resistance of a single cell.

FIG. 6 is a diagram showing an embodiment implementing a measurement circuit for measuring the complex resistance of a single cell.

The circuit shown in the figure is based on the IV method. In order to implement a multi-point frequency measurement carried out in a short period of time, a plurality of input voltages having frequencies different from each other are synthesized with each other by superposing the input voltages on each other and are applied between electrodes. A Fourier transform is subsequently applied to an output voltage and an output current in order to measure a complex resistance for every frequency. An electrode EL and the ground electrode G which are employed in the circuit shown in FIG. 6 correspond to respectively the electrode pairs EL1 and EL2 of the micro flow channel device MF shown in FIG. 4. In actuality, the ground electrode G is used as a common electrode.

As described before, in order to measure the complex resistance of a sample, it is necessary to measure both the voltage appearing between the two ends of the sample and the current flowing through the sample. The voltage of the sample is measured by a voltage receiving section VR shown in FIG. 6 whereas the current of the sample is measured by a current receiving section IR shown in the same figure.

Each of these voltage and current signals is amplified by an amplifier. Since the amplifier is combined with a band pass filter if necessary, each of the signals does not necessarily represent a single cell. A signal including a plurality of components having frequencies different from each other is distributed by a distributor D1 or D2 to n sub-frequency bands. This is because it is difficult to make use of one analog circuit for processing the entire frequency band used for grasping a dielectric relaxation phenomenon of the cell. In any individual sub-frequency band i (where i=1, . . . n), an analog signal passing through an analog filter AFVi or AFIi composed of devices having characteristics proper for the band is converted by an analog/digital converter ADi into a digital signal. The digital signal obtained as the result of the conversion is processed by a digital-signal processing circuit DPi. Finally, by synthesizing signals from all sub-frequency bands, a dispersion of the complex resistances throughout all the sub-frequency bands is measured.

[Data Analyses]

The measured dispersion of the complex resistance is analyzed typically at five stages described as follows.

(1) Conversion of Measured Data

The measured complex resistances are calibrated by taking the transmission characteristic of the measurement system into consideration. From the calibrated complex resistances, the electrical capacitance C of the sample and the conductance G of the sample are obtained. In the following description, the electrical capacitance C and the conductance G are referred to as CG data of the sample.

(2) Extraction of a Signal Originated from the Cell

At a specific frequency point, a signal of a cell is extracted from the CG data depending on the time. That is to say, a peak is extracted from the CG data whereas a base line is calculated from data before and after the peak. Then, a difference between the value of the peak and the base line is computed in order to find changes $\Delta C$ of the capacitance C and changes $\Delta G$ of the conductance G at all frequency points. In the following description, the changes $\Delta C$ and the changes $\Delta G$ are referred to as $\Delta C \Delta G$ data.

(3) Calculation of Dielectric Variables

By adoption of a numerical-value computation method taking the configuration of the stenosis channel NC serving as the signal detection section into consideration, a distribution of the $\Delta C \Delta G$ data for every cell is converted into a frequency dispersion of the dielectric constant $\epsilon$ and the specific electric conductivity $\kappa$. In the following description, the dielectric constant $\epsilon$ and the specific electric conductivity $\kappa$ are referred to as $\epsilon \kappa$ data. The frequency dispersion of the $\epsilon \kappa$ data is a dielectric dispersion. By applying a dielectric function to the dielectric dispersion for every cell, dielectric variables can be calculated.

(4) Calculation of the Electrical Physicality Value of the Cell Configuration Facet A relation table computed in advance is referred to in order to calculate the electrical physicality value of the cell configuration facet from the dielectric variables.

(5) Cell Classification Based on the Electrical Physicality Value

The distributions of the electrical physicality value for detected cells are classified into proper and small cell groups each representing one of cell types. Then, for each of the cell types, quantities such as the average and variance of the electrical physicality values are calculated.

Measured Data

As measured data, data for a K562 cell and a Jurkat cell is taken as an example. The K562 cell is a cultured cell line caused by the human erythroblastoid leukemia disease whereas the Jurkat cell is a cultured cell line caused by a lymphocyte tumor of the human leukemia disease T.

Figure 7:
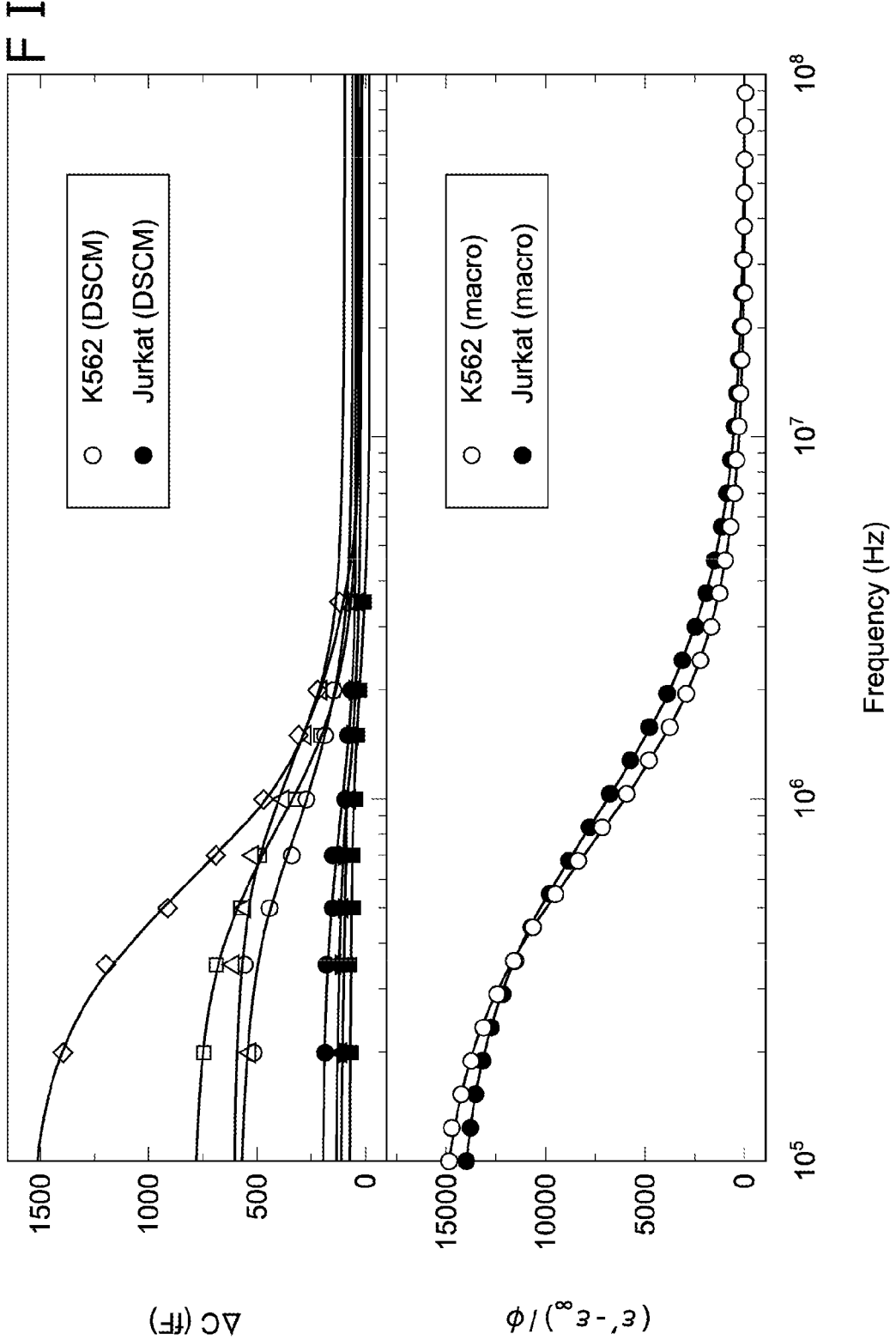
FIG. 7 shows a plurality of diagrams illustrating frequency characteristics; a graph on the upper side of FIG. 7 represent results of measurements carried out by the dielectric spectro cytometric apparatus whereas a graph shown on the lower side of FIG. 7 represents dispersions of the complex dielectric constants of a K562 cell and a Jurkat cell.

A graph on the upper side of FIG. 7 represent results of measurements carried out by the dielectric spectro cytometric apparatus 300. Data points represented by different symbols on the graph depend on different cells. That is to say, the graph is plotted to represent pieces of data at eight frequency points for a single cell. The graph show results of adapting data points to a relaxation function.

The vertical axis for the graph on the upper side of FIG. 7 represents the electrical-capacitance change computed from the measured complex resistance. In accordance with the data analysis method already described earlier, the electrical-capacitance change can be converted into the real part of a complex dielectric constant. By merely changing the scale of the vertical axis, however, there is virtually no difference. Thus, the change $\Delta C$ of the electrical capacitance is shown as it is. Data computed from the imaginary part of the complex dielectric constant as data representing the conductance G is also obtained but not shown in the figure. The imaginary part of the complex dielectric constant is the complex resistance.

On the other hand, a graph on the lower side of FIG. 7 represent the real part of the dispersion of the dielectric constant of the liquid solution for the K562 and Jurkat cells in the same way as the graph on the upper side. The liquid solution includes about $10^8$ cells. That is to say, the graph on the upper side of FIG. 7 represents data for a single cell whereas the graph on the lower side of the same figure represent averages of data for a number of cells. Thus, data adapted to a relaxation function is obtained, obviously making it possible to implement a quantitative measurement of the dielectric constant for a single cell. That is to say, it is now obvious that the dielectric spectro cytometry can be realized.

Figure 8:
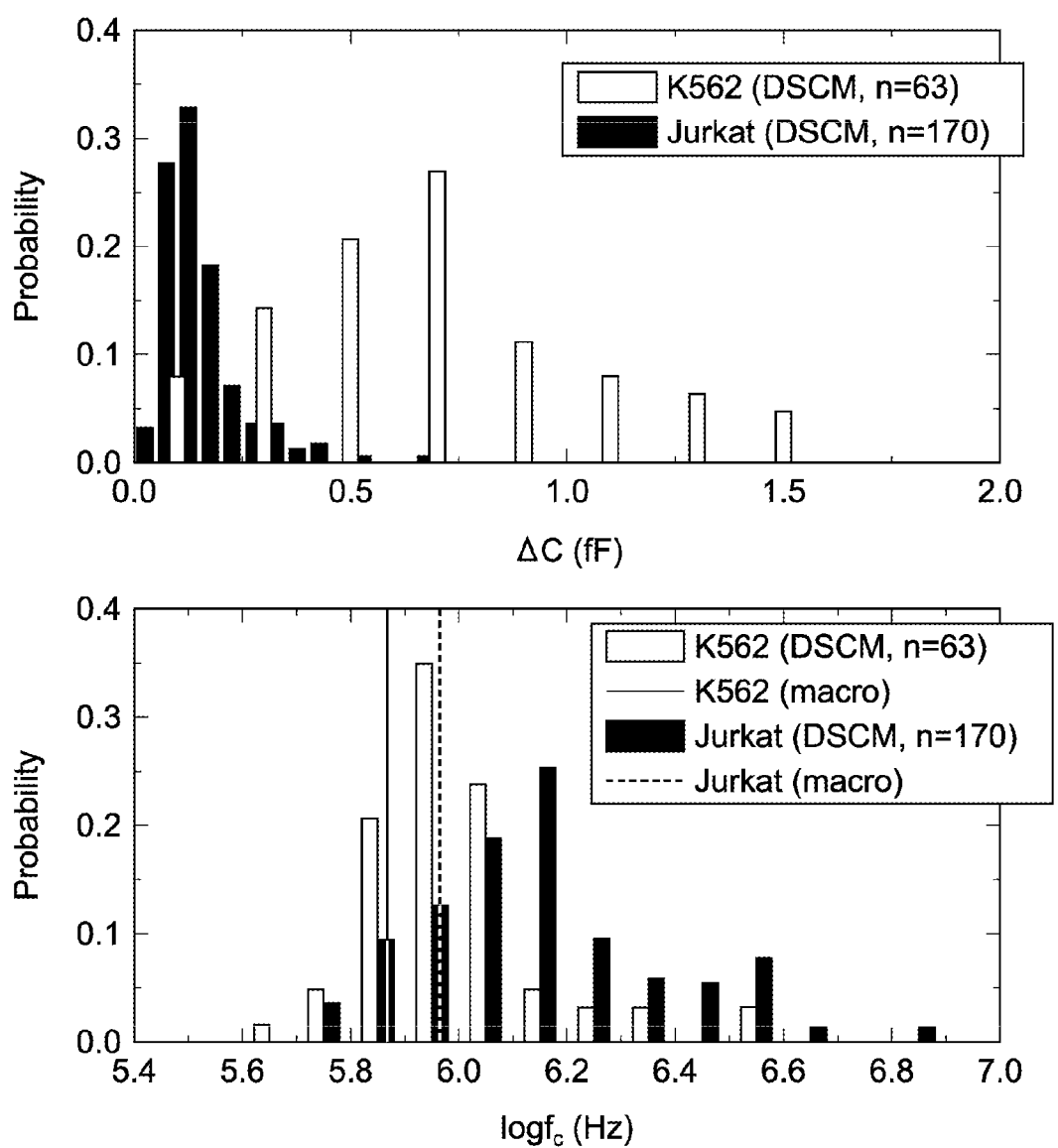
FIG. 8 is a set of histograms showing a dielectric variable obtained by adaption of the complex dielectric constant dispersion of a single cell to a relaxation function; that is to say.

FIG. 8 is a set of histograms showing a dielectric variable obtained by adaption of the complex dielectric constant dispersion of a single cell to a relaxation function. That is to say, FIG. 8 is a set of histograms showing $\Delta C$ representing a relaxation amplitude and a critical frequency fc at which the relaxation occurs. The figure shows different distributions of the dielectric variable for different cultured cells which are the K562 and Jurkat cells described above. The figure thus indicates that the dielectric spectro cytometry is capable of classifying cells into different cell types.

[Cell Sorting System]

Figure 9:
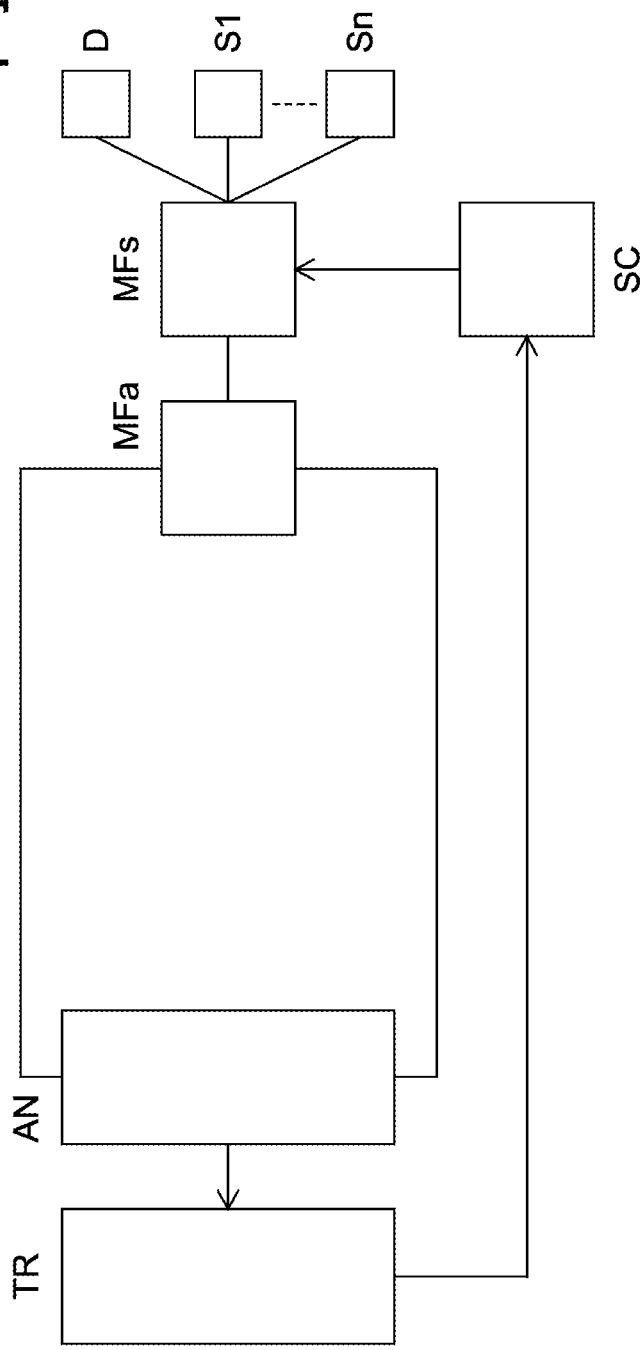
FIG. 9 is a block diagram showing the configuration of a cell sorting system.

FIG. 9 is a block diagram showing the configuration of a cell sorting system.

When the sorting-signal generator TR which is the sorting-signal generator 306 shown in FIG. 2 receives a complex resistance (or a complex dielectric constant) from the complex analyzer AN which is the analyzer 307 shown in FIG. 2, a value measured at every frequency point is compared with reference information set in advance. The reference information set in advance is information including a complex resistance measured in the past for each cell at the frequency point. As an alternative, the reference information set in advance is information including a complex dielectric constant found on the basis of such a complex resistance. On the basis of the result of the comparison, the sorting-signal generator TR generates a sorting signal serving as a trigger signal for sorting cells.

For example, a sorting-signal generator TR determines whether or not the measured complex resistance or the measured complex dielectric constant falls within a range centered at the reference information set in advance to serve as information corresponding to the measured complex resistance or the measured complex dielectric constant respectively. If the measured complex resistance or the measured complex dielectric constant falls within the range, the sorting-signal generator TR generates a trigger signal. To put it concretely, on the basis of the logical product of information obtained as a result of the comparison, the sorting-signal generator TR determines whether or not the cell is to be taken as a subject of sorting. If the cell is to be sorted, the sorting-signal generator TR generates a trigger signal and outputs the trigger signal to the cell-sorting mechanism CS which is the cell sorting mechanism 305 shown in FIG. 2.

The cell-sorting mechanism CS receiving the trigger signal determines a proper timing with which a cell passes through the cell sorting section of the micro flow channel device MF. In the case of an embodiment to be described later, the cell-sorting mechanism CS receiving the trigger signal determines a proper timing with which a cell passes through a portion immediately preceding the branch channels and generates a driving force such as a dielectrophoretic force or a fluid force with the proper timing in order to change the channel through which the cell flows. Thus, the cell flows through a channel different from channels through which other cells flow and is held in a cell accumulator Si (where i=1, . . . , n).

[3] Explanation of Concrete Embodiments of the Dielectric Spectro Cytometric Apparatus

[Dielectric Spectro-Cytometric Apparatus]

Figure 10:
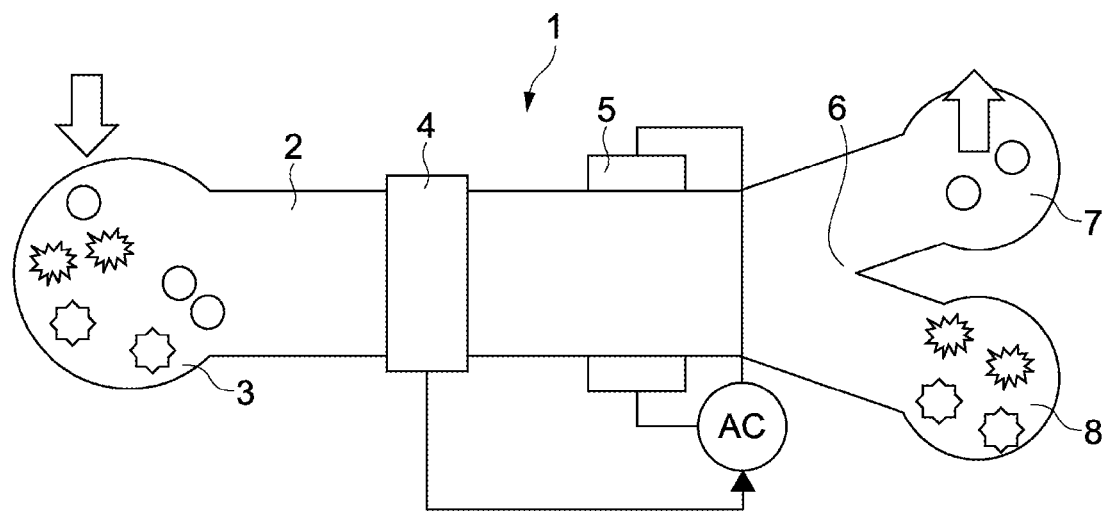
FIG. 10 is a diagram showing a model of a dielectric spectro-cytometric apparatus according to an embodiment of the present disclosure.
Figure 11:
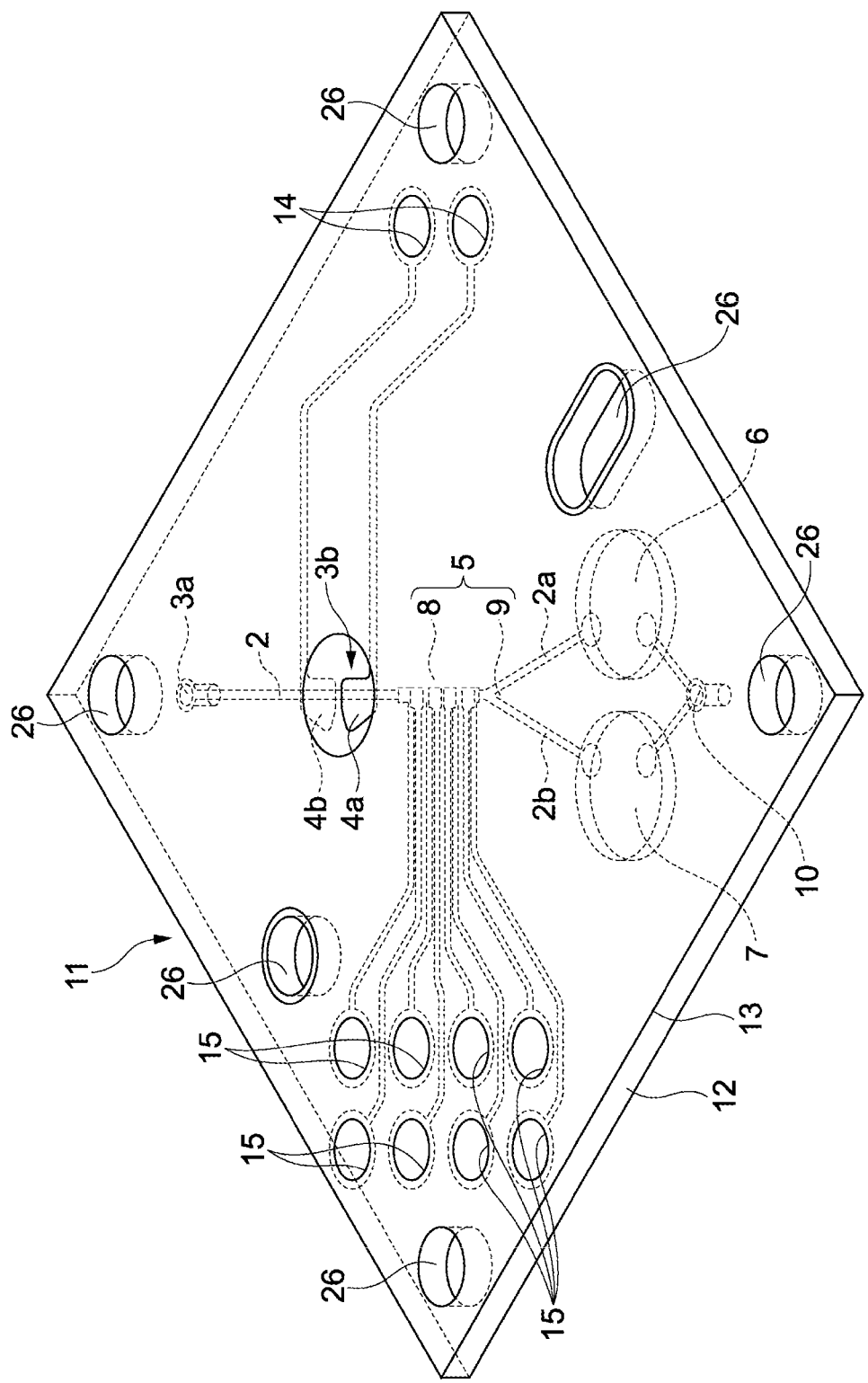
FIG. 11 is a perspective diagram showing a micro-flow-channel device included in the dielectric spectro cytometric apparatus shown in FIG. 10.

FIG. 10 is a diagram showing a model of a dielectric spectro-cytometric apparatus 300 according to an embodiment of the present disclosure whereas FIG. 11 is a perspective diagram showing a micro-flow-channel device MF included in the flow channel system 304 of the dielectric spectro cytometric apparatus 300 shown in FIG. 10. As shown in FIG. 2, the flow channel system 304 is included in the dielectric spectro cytometric apparatus 300.

As shown in FIG. 11, the micro flow channel device MF 11 has a substrate 12 and a member 13 made from a high-molecular film or the like to form the shape of a sheet. On the substrate 12, there are provided the flow channel 2, the branch channels 2a and 2b which are each a portion of the flow channel 2, a liquid injection section 3a functioning as the injection section 3, the flow splitting section 9 which is a portion of the flow channel 2, the cell fetching sections 6 and 7 as well as the outflow section 10. The flow channel 2, the branch channels 2a and 2b, the liquid injection section 3a, the flow splitting section 9, the cell fetching sections 6 and 7 as well as the outflow section 10 are constructed into a configuration provided on the substrate 12 by creating grooves or the like on the surface of the substrate 12 and by covering the surface with the member 13. In this way, the flow channel 2 is created.

The injection section 3 is a section for injecting liquid (or fluid) including a sampled cell by making use of a pressure control apparatus to be explained later by referring to typically FIG. 16 and figures subsequent to FIG. 16.

The liquid injected by the injection section 3 flows through the flow channel 2.

The measurement section 4 is a section for measuring the complex dielectric constant of a cell at frequency points in a frequency range of typically 0.1 MHz to 50 MHz for each individual cell flowing through the flow channel 2. The frequency range is a range in which the dielectric relaxation phenomenon of a cell occurs. The measurement section 4 measures the complex dielectric constant of a cell at typically three or more frequency points. For example, the measurement section 4 measures the complex dielectric constant of a cell at 10 to 20 frequency points. On the basis of the measured complex dielectric constants of a cell, the analyzer 307 including the measurement section 4 adopts the technique described before to determine whether or not the measured cell is a cell to be fetched from the micro flow channel device MF and to be used in an application such as an examination or a recycling process. If the analyzer 307 determines that the measured cell is a cell to be fetched from the micro flow channel device MF and to be used in such an application, the measurement section 4 generates a sorting signal.

It is to be noted that the measurement section 4 conceptually has the main function of the analyzer 307 described before and includes some of the mechanism of the flow channel system 304 also described before.

The cell sorting section 5 selects a desired cell from a plurality of cells injected by the injection section 3 as cells of different types and supplies the desired cell to the cell fetching section 6 and the other cells to the cell fetching section 7.

It is to be noted that the cell sorting section 5 conceptually has the main function of the sorting-signal generator 306 described before and includes some of the mechanism of the flow channel system 304 also described before.

An electric-field application section 8 provided in the cell sorting section 5 is a section capable of applying an electric field having a gradient in a direction different from the X direction in which the fluid flows. For example, the electric-field application section 8 is capable of applying an electric field having a gradient in a Y direction perpendicular to the X direction. Typically, when the cell sorting signal serving as a trigger signal is not received to become a generated operation signal, the electric-field application section 8 does not apply an electric field. When the cell sorting signal serving as a trigger signal is received to become a generated operation signal, on the other hand, the electric-field application section 8 applies an electric field. Of course, it is possible to provide a configuration in which, conversely, when the cell sorting signal serving as a trigger signal is received to become a generated operation signal, the electric-field application section 8 does not apply an electric field but, when the cell sorting signal serving as a trigger signal is not received to become a generated operation signal, on the other hand, the electric-field application section 8 applies an electric field.

A flow splitting section 9 of the cell sorting section 5 is a section for directing a cell to which the electric-field application section 8 does not apply the electric field to the cell fetching section 7 through a branch channel 2b and a cell experiencing the electric field generated by the electric-field application section 8 to the cell fetching section 6 through a branch channel 2a.

The cell fetching sections 6 and 7 are connected to the outflow section 10 through the flow channel 2. The fluid passing through the cell fetching sections 6 and 7 is exhausted by a pump from the outflow section 10 to an external destination.

[Micro-Flow-Channel Device]

As shown in FIG. 11, the micro flow channel device MF has a substrate 12 and a member 13 made from a high-molecular film or the like to form the shape of a sheet. On the substrate 12, there are provided the flow channel 2, the branch channels 2a and 2b which are each a portion of the flow channel 2, a liquid injection section 3a functioning as the injection section 3, the flow splitting section 9 which is a portion of the flow channel 2, the cell fetching sections 6 and 7 as well as the outflow section 10. The flow channel 2, the branch channels 2a and 2b, the liquid injection section 3a, the flow splitting section 9, the cell fetching sections 6 and 7 as well as the outflow section 10 are constructed into a configuration provided on the substrate 12 by creating grooves or the like on the surface of the substrate 12 and by covering the surface with the member 13. In this way, the flow channel 2 is created.

A cell injection section 3b into which the fluid including cells is injected is configured by providing a tiny hole on the member 13 to serve as a stenosis channel. When the fluid including cells is dropped on the cell injection section 3b by making use of a pipette, the fluid flows through the flow channel 2 to the downstream side of the flow channel 2 so that the fluid is mixed up with liquid flowing along the flow channel 2 through the stenosis channel. Since the stenosis channel is a tiny hole, cells never flow through the stenosis channel to the flow channel 2 as a group. Instead, a single cell is capable of passing through the stenosis channel sequentially one cell after another to the flow channel 2.

A pair of measurement electrodes 4a and 4b for measuring a complex resistance or a complex dielectric constant is provided to sandwich the stenosis channel. The pair of measurement electrodes 4a and 4b is provided to serve as a first electrode pair. The measurement electrode 4a which is a specific one of the electrodes is provided on the front face of the member 13 having a sheet shape whereas the measurement electrode 4b serving as the other electrode is provided on the rear face of the member 13 having a sheet shape.

An electrode pair composing the electric-field application section 8 is also provided on the rear face of the sheet-shaped member 13. This electrode pair will be described later.

The cell fetching sections 6 and 7 are covered by the sheet-shaped member 13 provided above the cell fetching sections 6 and 7. However, a cell can be fetched through a pipette by stinging the member 13 having a sheet shape with the pipette.

An electrode pad 14 is a section for fetching a signal detected by the measurement electrodes 4a and 4b and outputting the fetched signal to an external signal recipient. The fetched signal is also transmitted to the analyzer 307. An electrode pad 15 is a section for receiving an operation signal generated from a trigger signal based on measurement information of the complex dielectric constant of the analyzer 307 as a trigger. The trigger signal is the trigger signal generated by the sorting-signal generator 306. The received operation signal is transmitted to the electrode pair composing the electric-field application section 8 as described above.

A through hole 26 is a hole which is used for determining a position at which the micro flow channel device MF 11 is connected to the main body having the analyzer and other sections in the apparatus.

[Cell Sorting Section]

Figure 12:
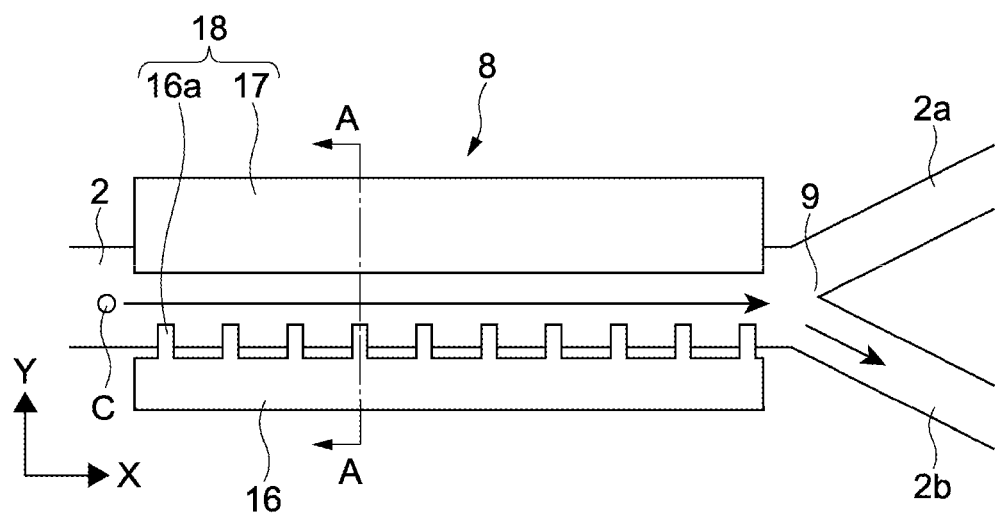
FIG. 12 is a diagram showing the top view of the configuration of a cell sorting section employed in the micro-flow-channel device shown in FIG. 11.
Figure 13:
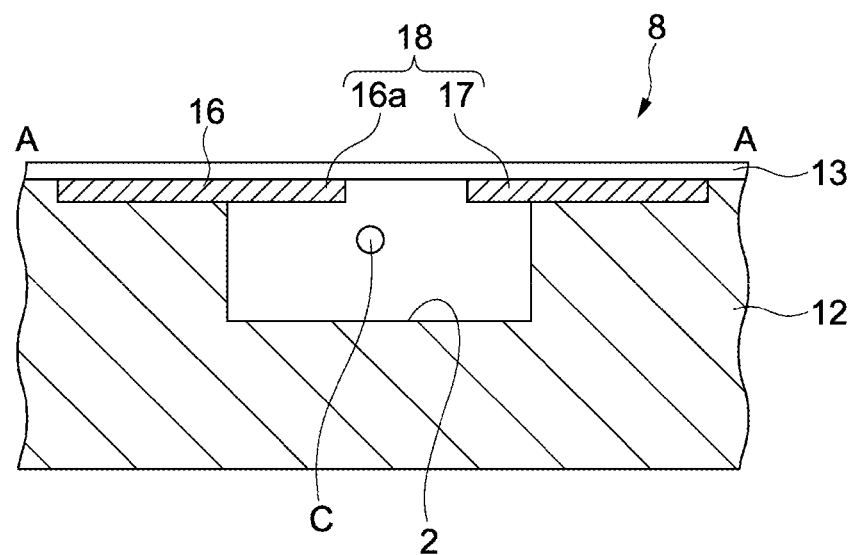
FIG. 13 is a diagram showing a cross section along a line A-A of the configuration of the cell sorting section shown in FIG. 12.

FIG. 12 is a diagram showing the top view of the configuration of a cell sorting section 5 employed in the micro-flow-channel device MF shown in FIG. 11 whereas FIG. 13 is a diagram showing a cross section along a line A-A of the configuration of the cell sorting section 5 shown in FIG. 12.

As shown in FIGS. 12 and 13, the cell sorting section 5 has the electric-field application section 8. The cell sorting section 5 is a section composing a portion of the cell sorting unit explained before.

The electric-field application section 8 has electrodes 16 and 17 each provided at a position determined in advance on the flow channel 2. For example, the electrodes 16 and 17 are provided at typically positions facing each other to sandwich the flow channel 2 in a Y direction different from an X direction in which the fluid flows through the flow channel 2.

The electrodes 16 and 17 are provided on the rear face of the member 13 having a sheet shape. The rear face of the member 13 is a ceiling face inside the flow channel 2. The electrode 16 is typically an electrode to which a signal is applied. The electrode 16 is configured to have a number of electrode pointers 16a each protruding in a direction toward the electrode 17. The electrode 17 is typically the common electrode. The electrode 17 is configured to have neither protrusions nor dents in a direction in which the electrode 17 faces the electrode 16. In the following description, a combination of one electrode pointer 16a and the electrode 17 is referred to as an operation-electrode pair 18 functioning as a second electrode pair.

With the operation-electrode pair 18 configured as described above, when a signal is applied to the electrodes 16 and 17, an electric field having a gradient in the Y direction is applied to each operation-electrode pair 18. A voltage signal used for generating such an electric field is obtained by typically superposing a DC bias voltage on an AC voltage.

At a position determined in advance on the downstream side of the electric-field application section 8 of the flow channel 2, a cell C whose flowing direction has been changed by a dielectrophoretic force generated by an electric field applied by the electric-field application section 8 is directed to the cell fetching section 6 by making use of the branch channel 2a.

For example, at the injection section 3, a cell is injected to a position sided to the cell fetching section 7. This cell injected to a position sided to the cell fetching section 7 is put in a non-active state and flows inside the flow channel 2 to the cell fetching section 7 through the position sided to the cell fetching section 7 by sustaining its flowing direction as it is and through the flow splitting section 9 to enter the branch channel 2b connected to the cell fetching section 7 as shown in FIG. 12. A non-active state is a state in which a cell not serving as the subject of cell sorting does not experience an electric field at the electric-field application section 8 when the cell is passing through the electric-field application section 8.

Figure 14:
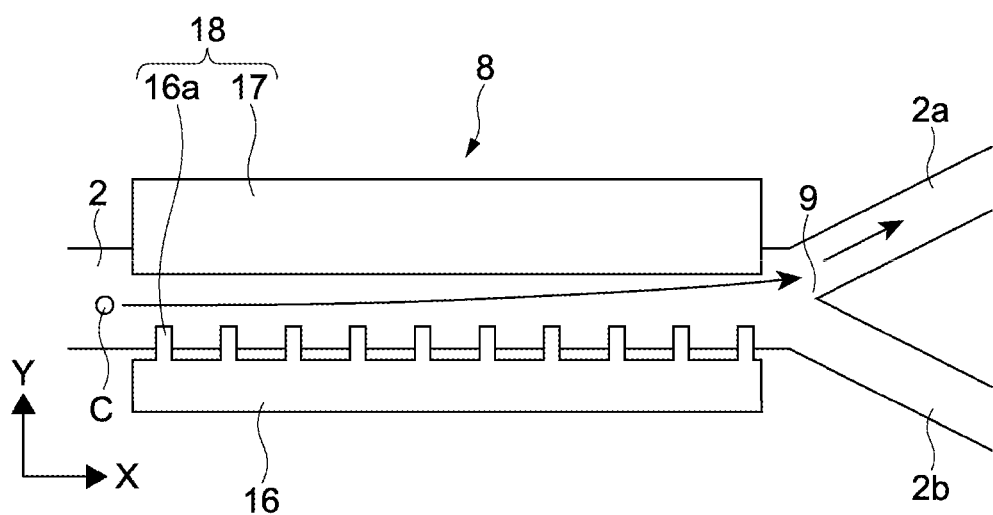
FIG. 14 is a diagram showing a state in which an electric field is applied to an electric-field application section and in order to change the direction in which a cell flows.

If the cell injected to a position sided to the cell fetching section 7 is put in an active state, however, the cell flows inside the flow channel 2 through the position sided to the cell fetching section 7 by changing its flowing direction to the cell fetching section 6 and through the flow splitting section 9 to enter the branch channel 2a connected to the cell fetching section 6 as shown in FIG. 14. A non-active state is a state in which a cell serving as the subject of cell sorting experiences a dielectrophoretic force generated by an electric field applied by the electric-field application section 8 when the cell is passing through the electric-field application section 8.

In the electric-field application section 8 configured as described above, each operation-electrode pair 18 applies an electric field having a gradient in the Y direction. Thus, a cell passing through a operation-electrode pair 18 gradually changes its flow channel and branches to the side of the cell fetching section 6 by flowing through the branch channel 2a.

[Other Embodiments of the Electric-Field Applying Section]

The dielectrophoretic force applied to a cell in an electric field having a strength not causing a fatal damage to the cell is generally extremely small in comparison with a viscosity resistance force applied to a cell flowing through water at a velocity of the order of several mm/s. Thus, it is necessary to provide a number of non-uniform electric fields each used for deliberately generating a dielectrophoretic force in a direction perpendicular to the flowing direction or a number of electrode-pair columns each consisting of operation-electrode pairs 18 each used for generating such an electric field. In this case, the columns are each provided in the X direction. As shown in FIGS. 12 and 14, if a voltage is applied to the numerous operation-electrode pairs 18 at the same time, an electrode column sorting area of the operation-electrode pairs 18 must be used exclusively so that the throughput does not increase in some cases.

Figure 15:
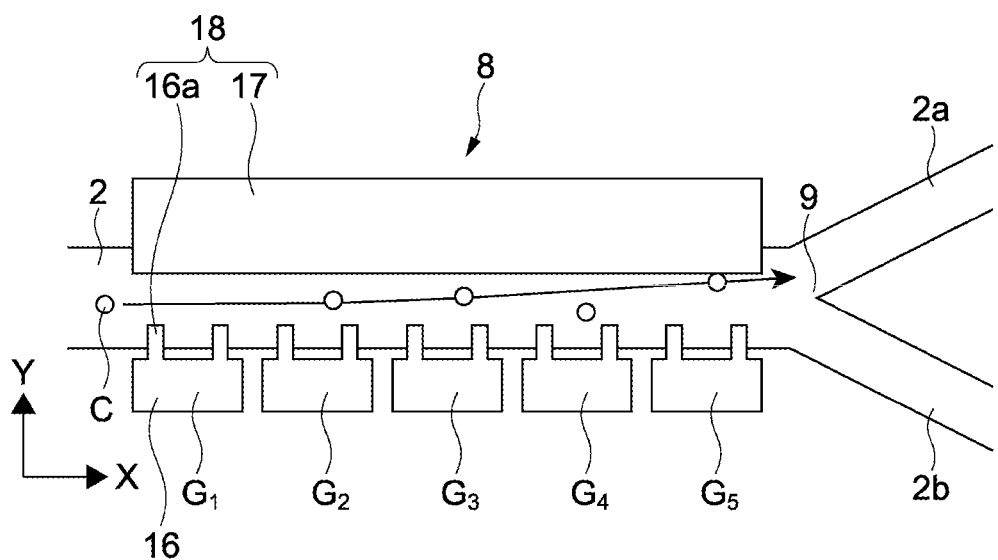
FIG. 15 is a diagram showing the configuration of a cell sorting section according to another embodiment.

In order to solve the problem described above, the operation-electrode pairs 18 are divided into a plurality of groups such as groups G1 to G5 arranged in the X direction as shown in FIG. 15 and a voltage applied individually to each of the groups G1 to G5 is controlled in order to allow multiplexing of cells passing through the operation-electrode pairs 18. In this way, the throughput can be increased. That is to say, in the case of the electric-field application section 8 having a configuration shown in FIGS. 12 and 14, it is necessary to let a cell flow to the flow channel 2 with such a timing that, till a specific cell passes through the electric-field application section 8, a cell coming after the specific cell is prevented from flowing to the flow channel 2. In the case of the electric-field application section 8 having a configuration shown in FIG. 15, on the other hand, it is possible to carry out control to apply an electric field to, for example, a cell currently passing through a group G5 but apply no electric field to a cell currently passing through a group G4. As a result, it is possible to carry out sorting control on each of the groups G1 to G5.

[Pressure Control of Flow Channel System]

The following description explains a pressure control apparatus for carrying out pressure control on fluid flowing inside the flow channel system 304.

Figure 16:
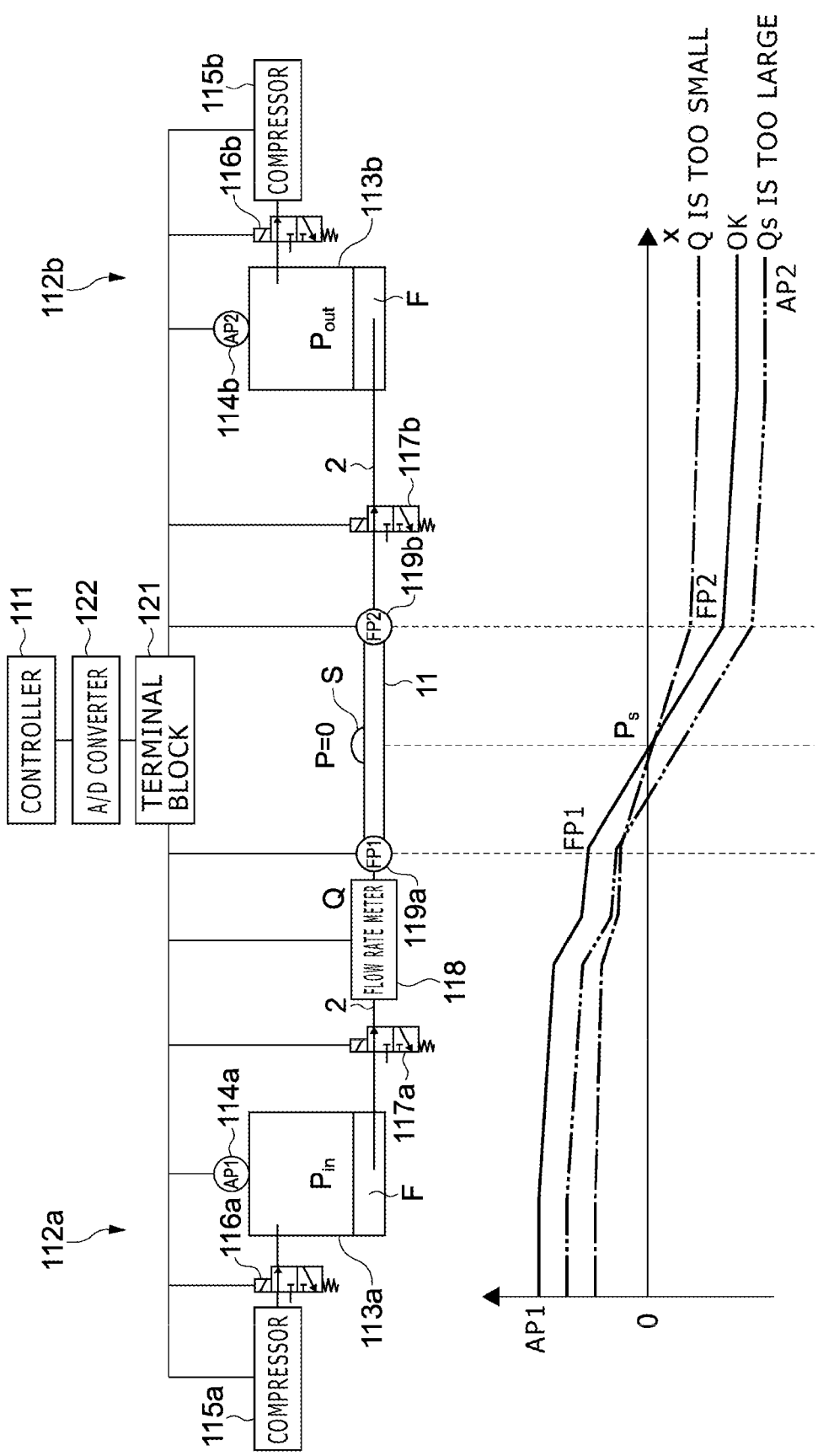
FIG. 16 is a diagram showing a pressure control apparatus for carrying out pressure control on fluid flowing through the inside of the flow channel system.
Figure 17:
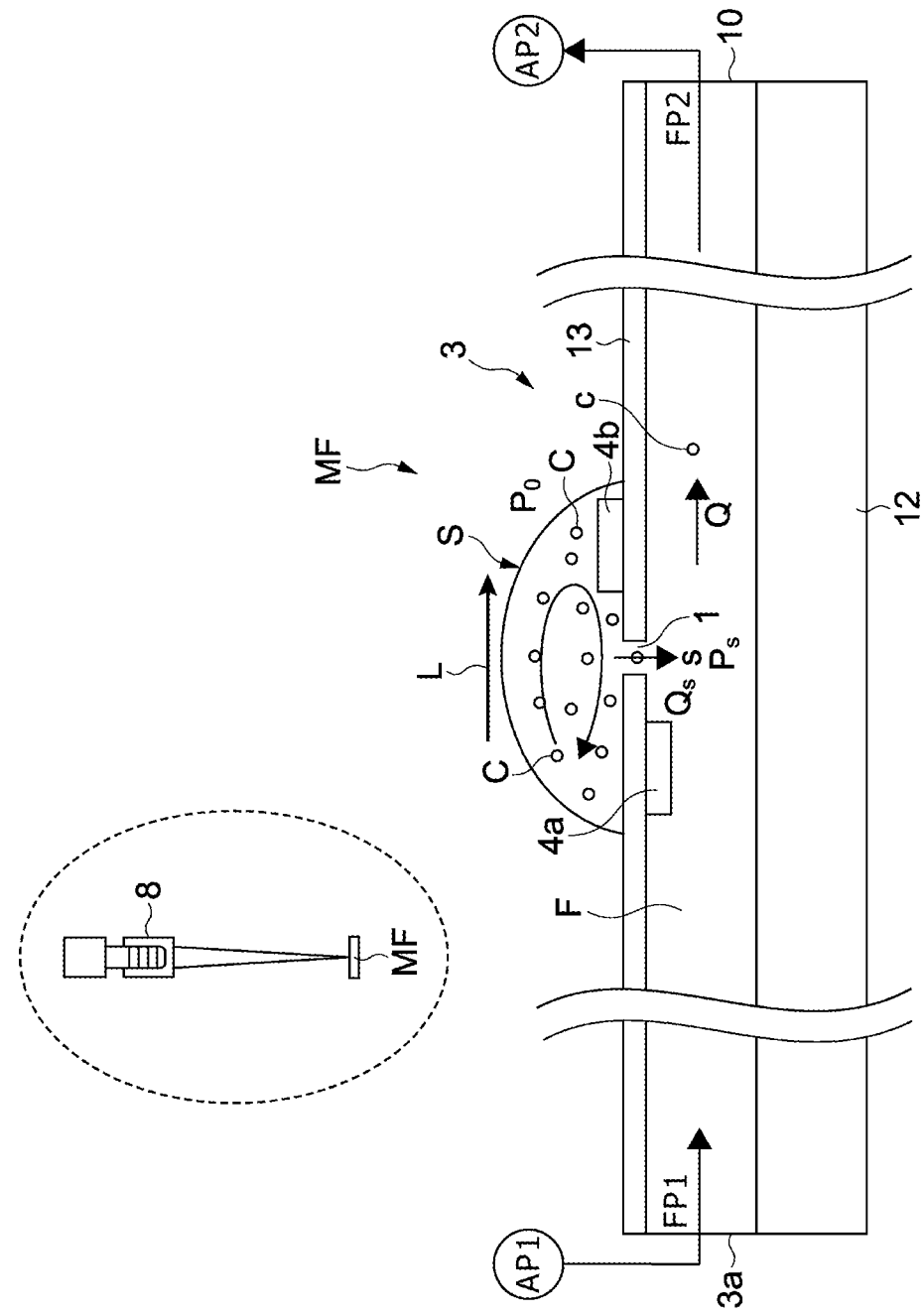
FIG. 17 is a diagram showing a model of a cross section of the neighborhood of an injection section employed in the micro-flow-channel device.

FIG. 16 is a diagram showing a pressure control apparatus for carrying out pressure control on fluid flowing through the inside of the flow channel system 304. FIG. 16 also shows gage pressures at a variety of locations in the flow channel system 304. FIG. 17 is a diagram showing a model of a cross section of the neighborhood of an injection section 3 employed in the micro-flow-channel device MF.

As shown in FIG. 16, the pressure control apparatus has a first pressure adjustment mechanism 112a and a second pressure adjustment mechanism 112b. The first pressure adjustment mechanism 112a is a mechanism for adjusting the pressure of carrier fluid F on the upstream side of the flow channel 2 whereas the second pressure adjustment mechanism 112b is a mechanism for adjusting the pressure of carrier fluid F on the downstream side of the flow channel 2. The carrier fluid F is a fluid part injected from the liquid injection section 3a.

In addition, the pressure control apparatus also has a controller 111 for controlling the first pressure adjustment mechanism 112a and the second pressure adjustment mechanism 112b.

The first pressure adjustment mechanism 112a includes a high-pressure fluid tank 113a, a first compressor 115a and a first air valve 116a provided between the high-pressure fluid tank 113a and the first compressor 115a. By the same token, the second pressure adjustment mechanism 112b includes a low-pressure fluid tank 113b, a second compressor 115b and a second air valve 116b provided between the low-pressure fluid tank 113b and the second compressor 115b.

The high-pressure fluid tank 113a is a component for accumulating carrier fluid F in the inside thereof as carrier fluid F to be supplied to the flow channel 2. On the other hand, the low-pressure fluid tank 113b is a component for accumulating carrier fluid F, which has been exhausted from the flow channel 2, in the inside thereof. The high-pressure fluid tank 113a is provided with a pressure sensor 114a for detecting the atmospheric pressure inside the high-pressure fluid tank 113a. By the same token, the low-pressure fluid tank 113b is provided with a pressure sensor 114b for detecting the atmospheric pressure inside the low-pressure fluid tank 113b.

A first valve 117a is provided on the downstream side of the high-pressure fluid tank 113a whereas a second valve 117b is provided on the upstream side of the low-pressure fluid tank 113b.

A flow meter 118 is provided on the downstream side of the first valve 117a. In addition, a pressure sensor 119a and a pressure sensor 119b are provided on the liquid injection section 3a of the micro flow channel device MF and the outflow section 10 of the micro flow channel device MF respectively. Each of the pressure sensor 119a and the pressure sensor 119b is used for detecting the pressure of the carrier fluid F.

The controller 111 is electrically connected to, among others, components included in a pressure adjustment mechanism 112, the flow meter 118 as well as the pressure sensors 119a and 119b through a terminal block 121 and an A/D converter 122.

The controller 111 controls an operation to drive the first compressor 115a and an operation to adjust the degree of opening of the first air valve 116a in order to adjust the atmospheric pressure inside the high-pressure fluid tank 113a. By the same token, the controller 111 also controls an operation to drive the second compressor 115b and an operation to adjust the degree of opening of the second air valve 116b in order to adjust the atmospheric pressure inside the low-pressure fluid tank 113b. In this way, it is possible to adjust the pressure of the carrier fluid F on the upstream and downstream sides of the flow channel 2.

In addition, the controller 111 also controls an operation to adjust the degree of opening of the first valve 117a and an operation to adjust the degree of opening of the second valve 117b in order to adjust the discharging of the carrier fluid F from the high-pressure fluid tank 113a and the injection of the carrier fluid F into the low-pressure fluid tank 113b. If necessary, the first valve 117a and the second valve 117b are replaced with new ones for example when the micro flow channel device MF is mounted on the pressure control apparatus and dismounted from the pressure control apparatus.

As shown in FIG. 11, the injection section 3 of the micro flow channel device MF is created on the surface of the member 13 having a sheet shape at a level lower than the level of other components in a state of being dented. Sample fluid S in the injection section 3 shown in FIG. 17 is part of fluid including cells. A typical example of the sample fluid S is blood. With the micro flow channel device MF created as described above, when the sample fluid S is injected into the injection section 3 by making use of a pipette 8 or the like, it is possible to prevent the sample fluid S from undesirably protruding from the injection section 3.

A stenosis hole 1 serving as the stenosis channel is provided at about the center of the injection section 3. The stenosis hole 1 is a tiny hole formed through the member 13 having a sheet shape in the lateral direction.

The dielectric spectro cytometric apparatus 300 may also have an agitation section for agitating the sample fluid S injected into the injection section 3. The agitation section itself is not shown in the figure. The agitation section is a section for generating an airflow L and blowing the airflow L to the surface of the sample fluid S flowing through the stenosis hole 1 as shown in FIG. 17. Thus, since a cell C included in the sample fluid S is agitated, it is possible to prevent the cell C from undesirably sinking into the sample fluid S.

A pair of measurement electrodes 4a and 4b of the measurement section 4 are located at locations sandwiching the stenosis hole 1 on the injection section 3. The measurement electrode 4a of the measurement-electrode pair is provided on the rear face of the member 13 having a sheet shape whereas the measurement electrode 4b of the measurement-electrode pair is provided on the front face of the member 13.

Next, the following description explains adjustment based on control of the pressure of the carrier fluid F as adjustment of a main flow quantity Q and a sample flow-in quantity Qs. The main flow quantity Q is the flow quantity of the carrier fluid F flowing through the flow channel 2 whereas the sample flow-in quantity Qs is the flow quantity of sample fluid S flowing inside the flow channel 2 through the stenosis hole 1.

First of all, the reader is requested to assume a case in which the sample fluid S is not injected into the injection section 3 and the sample fluid S does not exists above the stenosis hole 1, that is, the sample fluid S does not exists on the air side. If the atmospheric pressures in the high-pressure fluid tank 113a and the low-pressure fluid tank 113b are held at AP1 and AP2 respectively where the relation AP1>AP2 holds true, the carrier fluid F flows out from the high-pressure fluid tank 113a and flows to the low-pressure fluid tank 113b through the flow channel 2. The quantity of the carrier fluid F flowing at that time is the main flow quantity Q.

Let the pressures measured at the liquid injection section 3a of the micro flow channel device MF and the outflow section 10 of the micro flow channel device MF be FP1 and FP2 respectively. In this case, a static pressure Ps at a location s right below the stenosis hole 1 is determined from the pressures FP1 and FP2. The static pressure Ps is determined on the basis of a pressure loss caused by a pipeline resistance reflecting the shape of the flow channel 2 inside the micro flow channel device MF.

It is to be noted that, at that time, in a range of relatively small magnitudes of the static pressure Ps, the carrier fluid F does not flow out from the stenosis hole 1 due to a surface tensile force as long as no sample fluid S exists above the stenosis hole 1, that is, as long as no sample fluid S exists on the air side. In addition, no gas flows into the flow channel 2.

The reader is requested to assume a case in which, in such a state, a drop of the sample fluid S such as blood falls on the injection section 3 as a drop having a size of about 10 µL. In this case, the sample fluid S is coming in contact with the air as before and the altitude of the injection section 3 is about 1 mm. Thus, the static pressure of the sample fluid S above the stenosis hole 1 can be regarded to be 0 which is the magnitude of the atmospheric pressure. In addition, the surface tensile force does not exist on the stenosis hole 1 at the earliest time. Thus, since the static pressure at the location s right below the stenosis hole 1 is Ps, a pressure difference of (0−Ps) causes the sample fluid S to flow into the flow channel 2. If the static pressure Ps at the location s right below the stenosis hole 1 is held at a negative value, the sample fluid S is pulled into the flow channel 2 of the micro flow channel device MF.

In general, the static pressure Ps is a function of pipeline resistance. Thus, Eq. (1) given below holds true:

$$Ps = f(FP1, FP2) \quad (1)$$

Accordingly, the sample flow-in quantity Qs can be expressed by Eq. (2) given below as long as the Reynolds number has a sufficiently small value. In Eq. (2), notation Rs denotes a constant of proportionality.

$$Qs = Rs f(FP1 - FP2) \quad (2)$$

It is to be noted that, for the flow channel 2 inside the micro flow channel device MF, if the upstream and downstream sides are made hydrodynamically symmetrical with respect to the location s right below the stenosis hole 1, the static pressure Ps at the location s can be made simpler and thus expressed by Eq. (3) as follows.

$$Ps = (FP1 + FP2)/2 \quad (3)$$

In addition, in this case, the sample flow-in quantity Qs is expressed by Eq. (4) as follows.

$$Qs = Rs(FP1 + FP2)/2 \quad (4)$$

On top of that, the main flow quantity Q can be found from the pressures FP1 and FP2 as well as the pipeline resistance R for the main flow in accordance with Eq. (5) given as follows.

$$Q = R(FP1 - FP2) \quad (5)$$

As described above, the pressure AP1 in the high-pressure fluid tank 113a and the pressure AP2 in the low-pressure fluid tank 113b are adjusted in order to properly adjust the pressure FP1 of the carrier fluid F on the upstream side of the flow channel 2 and the pressure FP1 of the carrier fluid F on the downstream side of the flow channel 2 so that each of the main flow quantity Q and the sample flow-in quantity Qs can be controlled to an arbitrary value. In addition, the pressure AP1 in the high-pressure fluid tank 113a and the pressure AP2 in the low-pressure fluid tank 113b are adjusted in order to properly adjust the pressure FP1 of the carrier fluid F on the upstream side of the flow channel 2 and the pressure FP1 of the carrier fluid F on the downstream side of the flow channel 2 so that the main flow quantity Q and the sample flow-in quantity Qs can be controlled independently of each other.

[Other Embodiments]

Implementations of the present disclosure are by no means limited to the embodiment described above. That is to say, a variety of other embodiments can be realized.

For example, in the embodiment described above, as a method for measuring a complex resistance, a method based on a multi-point frequency is adopted. However, the method based on a multi-point frequency is not necessarily adopted as the method for measuring a complex resistance.

In the embodiment described above, as a typical multi-point frequency measurement, the frequency superposition method is adopted. However, there are three other multi-point frequency measurement methods described below. Much like the frequency superposition method, in each of the three other multi-point frequency measurement methods, it is possible to determine a dispersion on a real-time basis every time a single cell passes through the stenosis channel NC.

(1) Frequency Sweeping Method

A frequency sweeping method is a method for measuring a complex resistance at every frequency point while sweeping frequencies.

(2) Time-Domain Measurement Method

A time-domain measurement method is a method for computing a complex resistance at every frequency point by applying a voltage having a pulse or step waveform to measurement electrodes, measuring voltage and current changes and carrying out a Fourier transform.

(3) Other Multi-point Frequency Measurement Method

In accordance with another multi-point frequency measurement method, measurement-electrode pairs are divided into a plurality of pair groups and measurements are carried out when a cell sequentially passes through the pair groups. This other multi-point frequency measurement method is not a method for measuring complex resistances at all measurement frequency points in a batch operation as is the case with the frequency superposition method described above. Instead, in the other multi-point frequency measurement method, for every group of measurement-electrode pairs, measurements are carried out on few frequency points such as one to three frequency points. By carrying out measurements on frequency points the number of which varies from group to group, as a whole, it is possible to implement the multi-point frequency method.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A dielectric cytometric apparatus comprising:
a flow channel including a stenosis channel through which a single cell is capable of flowing and branch channels provided on the downstream side of said stenosis channel as branch channels for sorting cells included in liquid flowing through said flow channel;
a first electrode pair capable of creating an alternating current electric field on said stenosis channel;
an analysis unit configured to measure a complex dielectric constant depending on said cell for each of said cells each flowing through said stenosis channel by creating said alternating current electric field on said stenosis channel through application of an alternating current voltage to said first electrode pair;
a second electrode pair capable of creating an electric field on a flow-channel portion on the downstream side of said stenosis channel but on the upstream side of said branch channels, wherein the second electrode pair comprises a first electrode which comprises electrode pointers, the electrode pointers each protruding in a direction towards a second electrode; and
a cell sorting unit configured to apply a dielectrophoretic force to said cells in order to sort said cells through use of said branch channels by driving said second electrode pair to create said electric field on the basis of said complex dielectric constant measured by said analysis unit.

2. The dielectric cytometric apparatus according to claim 1 wherein, as a signal of said alternating current voltage applied to said first electrode pair, said analysis unit generates a superposed voltage signal superposing an alternating current voltage having a plurality of frequencies and carries out a Fourier transform on signals of a voltage and a current, which are measured when said single cell passes through said stenosis channel, in order to calculate said complex dielectric constant for every one of said frequencies.

3. The dielectric cytometric apparatus according to claim 1 wherein:
said analysis unit stores in advance reference information to be used as a reference of said complex dielectric constant measured for each of said cells; and
said cell sorting unit refers to said complex dielectric constant measured by said analysis unit and said reference information on a real-time basis and creates said electric field on the basis of information indicating whether or not said complex dielectric constant is within a range of said reference information.

4. A dielectric cytometric cell sorting method including:
causing fluid including cells to flow through a flow channel including a stenosis channel and branch channels;
creating an alternating current electric field on said stenosis channel;
measuring a complex dielectric constant depending on said cell for each of said cells passing through said stenosis channel;
comparing the measured complex dielectric constant to reference information set in advance to determine if the measured complex dielectric constant falls within a range centered at the reference information set in advance;
generating a trigger signal if the measured complex dielectric constant falls within the range; and
creating an electric field on a flow-channel portion on the downstream side of said stenosis channel but on the upstream side of said branch channels on the basis of said measured complex dielectric constant in order to apply a dielectrophoretic force to said cells so that said cells can be sorted by making use of said branch channels.

5. The dielectric cytometric apparatus according to claim 1 wherein the analysis unit comprises a hardware control system, a software control system, and an analyzer.

6. The dielectric cytometric apparatus according to claim 1 wherein the first electrode of the second electrode pair comprises a plurality of distinct groups, each group comprising the electrode pointers.

* * * * *